(12) United States Patent
Panasyuk et al.

(10) Patent No.: US 8,644,911 B1
(45) Date of Patent: Feb. 4, 2014

(54) OXYVU-1 HYPERSPECTRAL TISSUE OXYGENATION (HTO) MEASUREMENT SYSTEM

(75) Inventors: Svetlana Panasyuk, Lexington, MA (US); Jenny Freeman, Weston, MA (US); Kevin Schomacker, Maynard, MA (US); Richard Lifsitz, Wellesley, MA (US)

(73) Assignee: Hypermed Imaging, Inc., Greenwich, CT (US)

( * ) Notice: Subject to any disclaimer, the term of this patent is extended or adjusted under 35 U.S.C. 154(b) by 1364 days.

(21) Appl. No.: 11/772,741

(22) Filed: Jul. 2, 2007

Related U.S. Application Data

(60) Provisional application No. 60/817,340, filed on Jun. 30, 2006.

(51) Int. Cl.
*A61B 6/00* (2006.01)

(52) U.S. Cl.
USPC .......................................... 600/473; 600/476

(58) Field of Classification Search
None
See application file for complete search history.

(56) References Cited

U.S. PATENT DOCUMENTS

| | | | |
|---|---|---|---|
| 6,198,532 B1 * | 3/2001 | Cabib et al. ................... | 356/456 |
| 2002/0154300 A1 * | 10/2002 | Mansfield et al. ............ | 356/300 |
| 2004/0236229 A1 * | 11/2004 | Freeman et al. .............. | 600/474 |
| 2005/0273011 A1 * | 12/2005 | Hattery et al. ................ | 600/476 |
| 2006/0173351 A1 * | 8/2006 | Marcotte et al. .............. | 600/473 |

* cited by examiner

Primary Examiner — Log V. Le
Assistant Examiner — Bradley Impink
(74) Attorney, Agent, or Firm — Brett A. Lovejoy; Andrew J. Antczak; Morgan, Lewis & Bockius LLP

(57) ABSTRACT

The invention is directed to a hyperspectral/multispectral system referred to as the OxyVu-1 system. The hyperspectral imaging technology performs spectral analysis at each point in a two-dimensional scanned area producing an image displaying information derived from the analysis. For the OxyVu-1 system, the spectral analytical methods determined in superficial tissues approximate values of oxygen saturation (HT-Sat), oxyhemoglobin levels (HT-oxy), and deoxyhemoglobin levels (HT-deoxy). The OxyVu-1 system displays the tissue oxygenation in a two-dimensional, color-coded image.

The system contains a system console, a cart, system electronics, CPU, monitor, keyboard, pointing device and printer. The hyperspectral instrument head with support arm contains broadband illuminator, camera and spectral filter for collecting hyperspectral imaging cube. The single use OxyVu Check Pads and Targets are used to perform an instrument check prior to patient measurements. The OxyVu Target is placed within the intended field of view and is used as a fiduciary mark for image registration and for focusing.

33 Claims, 17 Drawing Sheets

VISUAL IMAGE OF FOREARM

| SUBSYSTEM | TYPE | ABBR. | DESCRIPTION |
|---|---|---|---|
| PATIENT ID MODULE | APPLICATION | PIM | INCLUDES THE DEMOGRAPHIC INFORMATION ON THE PATIENT BEING STUDIED |
| CALIBRATION MODULE | APPLICATION | CM | PROVIDES FOR DARK REMOVAL, REFERENCE TO KNOWN CALIBRATION, REGISTRATION, DECOMPOSITION AND HIS CALCULATION |
| ACQUISITION MODULE | APPLICATION | AQM | PROVIDES FOR THE ACQUISITION OF SPATIAL AND CHEMICAL INFORMATION AT EACH SPECTRAL BANDWIDTH |
| ANALYSIS MODULE | APPLICATION | AM | INTERPRETS THE RESULTS OF THE SPATIAL AND CHEMICAL INFORMATION OBTAINED IN THE ACQUISITION MODULE |
| DISPLAY MODULE | APPLICATION | DM | DISPLAYS THE RESULTS OF THE ANALYSIS MODULE ON A COMPUTER MONITOR |
| DATA DELIVERY MODULE | APPLICATION | DDM | STORES THE ACQUIRED/PROCESSED DATA AND PRINTS THE HSI/VIS PICTURES |
| SYSTEM CONTROLLER | OPERATING SYSTEM | SC | COMMUNICATIONS INTERFACE BETWEEN THE SOFTWARE APPLICATION MODULES AND ALL DEVICE COMPONENTS |
| FILTER | DEVICE | F | LIQUID CRYSTAL SPECTRAL SEPARATOR |
| PRINTER | DEVICE | P | COLOR PRINTER TO RECORD INFORMATION FOR PATIENT'S PAPER CHART |
| MOUSE | DEVICE | P | METHOD OF CONTROLLING APPLICATION |
| CAMERA | DEVICE | C | MEASUREMENT ACQUISITION DEVICE |
| THERMOMETER | DEVICE | T | PROVIDES TEMPERATURE READINGS |
| KEYBOARD | DEVICE | K | DATA ENTRY DEVICE |

*FIG. 11*

OXYVU-1 HYPERSPECTRAL TISSUE OXYGENATION (HTO) MEASUREMENT SYSTEM

REFERENCE TO RELATED APPLICATIONS

This application claims priority to U.S. Provisional Application No. 60/817,340 entitled "OxyVu-1 Hyperspectral Tissue Oxygenation (HTO) Measurement System" filed Jun. 30, 2006, the entirety of which is hereby specifically incorporated by reference.

BACKGROUND

1. Field of the Invention

The invention is directed to methods and systems of hyperspectral and multispectral imaging of medical tissues. In particular, the invention is directed to new devices, tools and processes for the detection and evaluation of the physiological state of the tissue that incorporate hyperspectral/multispectral imaging.

2. Description of the Background

HSI or hyperspectral imaging is a novel method of "imaging spectroscopy" that generates a "gradient map" of a region of interest based on local chemical composition. HSI has been used in satellite investigation of suspected chemical weapons production areas, geological features, and the condition of agricultural fields and has recently been applied to the investigation of physiologic and pathologic changes in living tissue in animal and human studies to provide information as to the health or disease of tissue that is otherwise unavailable. MHSI for medical applications (MHSI) has been shown to accurately predict viability and survival of tissue deprived of adequate perfusion, and to differentiate diseased (e.g. tumor) and ischemic tissue from normal tissue.

Spectroscopy is used in medicine to monitor metabolic status in a variety of tissues. One of the most common spectroscopic applications is in pulse oximetry, which utilize the different oxyhemoglobin (oxyHb) and deoxyhemoglobin (deoxyHb) absorption bands to estimate arterial hemoglobin oxygen saturation. One of the drawbacks of these systems is that they provide no information about the spatial distribution or heterogeneity of the data. In addition, these systems report the ratio of oxyHb and deoxyHb together losing diagnostic information that can be garnered by evaluating the state of the individual components. Such spatial information for the individual components and the ratio is provided by HSI, which is considered a method of "imaging spectroscopy," where the multi-dimensional (spatial and spectral) data are represented in what is called a "hypercube." The spectrum of reflected light is acquired for each pixel in a region, and each such spectrum is subjected to standard analysis. This allows the creation of an image based on the metabolic state of the region of interest (ROI).

In vivo, MHSI has been used to demonstrate otherwise unobserved changes in pathophysiology. Specific studies have evaluated the macroscopic distribution of skin oxygen saturation, the in-situ detection of tumor during breast cancer resection in the rat, the determination of tissue viability following plastic surgery and burns, claudication and foot ulcers in diabetic patients, and applications to shock and lower body negative pressure (LBNP) in pigs and humans, respectively. In a skin pedicle flap model in the rat, tissue that has insufficient oxygenation to remain viable is readily apparent from local oxygen saturation maps calculated from hyperspectral images acquired immediately following surgery; by contrast, clinical signs of impending necrosis do not become apparent for 12 hours after surgery.

Non-invasive measurements of oxygen or blood flow have been demonstrated previously, with investigators using thermometry, point diffuse reflectance spectroscopy, and laser Doppler imaging. Sheffield et al, have also reviewed laser Doppler and $TcPO_2$ measurements and their specific applications to wound healing. While other techniques have been utilized in both the research lab and the clinic and have the advantage of a longer experience base, MHSI is superior to other technologies and can provide predictive information on the onset and outcomes of diabetic foot ulcers, venous stasis ulcers and peripheral vascular disease.

Because MHSI has the ability to show anatomically relevant information that is useful in the assessment of local, regional and systemic disease. This is important in the assessment of people with diabetes and/or peripheral vascular disease. MHSI shows the oxygen delivery and oxygen extraction of each pixel in the image collected. These images with pixels ranging from 20 microns to 120 microns have been useful in several ways. In the case of systemic disease, MHSI shows the effects on the microcirculation of systemic diabetes, smoking, a variety of medications such as all of the classes of antihypertensives (ACE inhibitors, ARBs, Beta blockers, Peripheral arterial and arteriolar dilators), vasodilators (such as nitroglycerine, quinine, morphine), vasoconstrictors (including coffee, tobacco, pseudephedrine, Ritalin, epinephrine, levophedrine, neosynepherine), state of hydration, state of cardiac function (baseline, exercise, congestive heart failure), systemic infection or sepsis as well as other viral or bacterial infections and parasitic diseases. The size of the pixels used is important in that it is smaller than the spacing of the perforating arterioles (~0.8 mm) of the dermis and therefore permits the visualization of the distribution of mottling or other patterns associated with the anatomy of the microcirculation and its responses. In the case of the use of MHSI for regional assessment, in addition to the above systemic effects at play, the image delivers information about the oxygen delivery and oxygen extraction for a particular region as it is influenced by blood flow through the larger vessels of that region of the body. For example an image of the top of the foot reflects both the systemic microvascular status and the status of the large (macrovascular) vessels supplying the leg. This can reflect atherosclerotic or other blockage of the vessel, potential injury to the vessel with narrowing, or spasm of some of the smaller vessels. It can also reflect other regionalized processes such as neuropathy or venous occlusion or compromise or stasis. In the case of local disease MHSI shows the actual effect of the combination of systemic, regional and local effects on small pieces of tissue. This combines the effects of systemic and regional effects described above with the effects of local influences on the tissue including pressure, neuropathy, localized small vessel occlusion, localized trauma or wounding, pressure sore, inflammation, and wound healing. Angiogenesis is readily monitored with MHSI.

The major clinical advantage of hyperspectral imaging is the delivery of metabolic information derived from the tissue's spectral properties in an easily interpretable image format with high spatial resolution. This 2-D information allows gradients in biomarker levels to be assessed spatially. Multiple images taken over time allow the gradient to be measured temporally. This adds new dimensions to the assessment of ulceration risk and tissue healing in that it will allow the physician to target therapy and care to specific at risk areas much earlier than previously possible. The reporting of biomarkers such as oxyHb and deoxyHb levels in tissue individually and in an image format where spatial distributions can be assessed has not been done before. Typically the two numbers are combined in a ratio and reported as percent hemoglobin oxygen saturation ($O_2$Sat). MHSI has the clear potential to be developed into a cost effective, easy to use, turn-key camera-based metabolic sensor given the availability and relatively low price of components.

There are many advantages to using MHSI. Not only does MHSI provide anatomically relevant spectral information, its use of spectral data of reflected electro-magnetic radiation (ultraviolet—UV, visible, near infrared—NIR, and infrared—IR) provides detailed tissue information. Since different types of tissue reflect, absorb, and scatter light differently, in theory the hyperspectral cubes contain enough information to differentiate between tissue types and conditions. MHSI is more robust than conventional analyses since it is based on a few general properties of the spectral profiles (slope, offset, water, oxyHb, deoxyHb, and its ratio) and is therefore flexible with respect to spectral coverage and not sensitive to a particular light wavelength. MHSI is faster than conventional analyses because it uses fast image processing techniques that allow superposition of absorbance, scattering, and oxygenation information in one pseudo-color image. Visible MHSI is useful because it clearly depicts oxyHb and deoxyHb which are important, physiologically relevant biomarkers in a spatially relevant fashion. Similarly, NIR shows water, oxyHb and deoxyHb.

The simplicity of the presented false color images representing distribution of various chemical species, either singly or in combination (such as ratioed), or in other more sophisticated image processing techniques allow for the display of results in real to near-real time. Another advantage of MHSI is easy interpretation. Color changes show the different tissue types or condition, but the distinction is not a yes/no type. MHSI color scheme allows the surgeon or podiatrist to differentiate between different tissue types and states. In addition, the color and the shape of structures depict different composition and level of viability of the tissue. The data is then represented in a developed MHSI standard format. OxyHb and deoxyHb are presented in a format similar to a blood pressure reading that is easy for physicians to understand. Additionally, a tissue oxygen saturation value denoted as $S_{HSI}O_2$ is also provided.

MHSI main purposes include 1) expand human capabilities beyond the ordinary array of senses; 2) expand the human brain capabilities by pre-analyzing the spectral characteristics of the observable subject; 3) perform these tasks with real or near-real time data acquisition. In summary, the aim of MHSI is to facilitate the diagnosis and assessment of the metabolic state of tissue.

Results of analysis have to be presented in an easily accessible and interpretable form. MHSI delivers results in an intuitive form by pairing MHSI pseudo-color image with a high quality color picture composed from the same hyperspectral data. Identification and assessment of a region of interest (ROI) is easily achieved by flipping between color and MHSI images, and zooming onto the ROI. The images can be seen on a computer screen or projector, and/or stored and transported as any other digital information, and/or printed out. The MHSI image preserves the high resolution of the hyperspectral imager thereby allowing further improvement with upgraded hardware.

Additionally, MHSI transcribes vast 3D spectral information sets into one image preserving biological complexity via millions of color shades. The particular color and distinct shape of features in the pseudo-color image allow discrimination between tissue types such as ulcers, callus, intact skin, hematoma, and superficial blood vessels.

Initially, the algorithm presents oxyHb, deoxyHb and $S_{HSI}O_2$ to the user to conclude characteristics of the tissue including, but not limited to, discerning whether the tissue is healing or whether it is at a high risk of ulceration. In another embodiment, a particular color code contains adequate information for diagnosis and is presented as such. In one iteration, MHSI by itself is not a definite decision making algorithm; it is a tool that a medical professional can use in order to give a confident diagnosis. In another iteration, MHSI contains a decision making algorithm that provides the physician with a diagnosis.

Due to the complexity of the biological system, medical personnel desire as much information as possible in order to make the most-reliable diagnosis. MHSI provides currently unavailable information to the doctor, preferably to be used in conjunction with other clinical assessments to provide an accurate diagnosis. MHSI provides images for further analysis by the user. As more information is gathered, a spectral library is preferably compiled to allow MHSI to be a true diagnostic device.

SUMMARY OF THE INVENTION

The present invention overcomes the problems and disadvantages associated with current strategies and designs and provides new tools and methods for hyperspectral/multispectral imaging and analysis as an oxygenation measurement system.

One embodiment of the invention is directed to a non-invasive, tissue oxygenation measurement system comprising a hyperspectral/multispectral imaging camera that reports an approximate value of: oxygen saturation, oxyhemoglobin level, and deoxyhemoglobin level in superficial tissue; a display for projecting two-dimensional color-coded images of tissue oxygenation of a scanned surface of one or more regions of the superficial tissue.

Another embodiment of the invention is directed to a system, wherein the oxygenation measurements comprise one or more of: a value for oxyhemoglobin, a value for deoxyhemoglobin, and a value for percent oxygen saturation.

Another embodiment of the invention is directed to a system, wherein tissue oxygenation information can be viewed pixel-by-pixel, as a region of interest, or for a viewing area.

Another embodiment of the invention is directed to a system, further comprising one or more of a system console, a cart, system electronics, CPU, monitor, keyboard, pointing device and printer.

Another embodiment of the invention is directed to a system comprising a hyperspectral instrument head with a support arm, wherein the hyperspectral instrument head contains a broadband illuminator, the camera, and a spectral filter for collecting a three-dimensional matrix of spectral measurements in the form of a hyperspectral imaging cube.

Another embodiment of the invention is directed to a system, wherein the two-dimensional images projected onto the display have a 0.1 mm spatial resolution within a 10 cm by 13 cm field of view.

Another embodiment of the invention is directed to a system further comprising a check pad and target, wherein the target is placed within an intended field of view and is used as a fiduciary mark for image registration and for focusing.

Another embodiment of the invention is directed to a system, wherein the system provides a tissue oxygenation scan with a 50 micron, 100 micron, 150 micron or 200 micron resolution.

Another embodiment of the invention is directed to a system, wherein the system performs the tissue oxygenation measurement in less than 20 seconds per site, less than 15 seconds, less than 10 seconds, less than 5 seconds, or within 2 seconds.

Another embodiment of the invention is directed to a system, wherein a patient is not physically contacted by any part of the system.

Another embodiment of the invention is directed to a system, wherein the tissue comprises or is near a wound or ulcer.

Another embodiment of the invention is directed to a system, wherein the system detects reduced blood flow ischemia states.

Another embodiment of the invention is directed to a system, wherein the hyperspectral instrument head is 17 inches from the tissue.

Another embodiment of the invention is directed to a system, further comprising a hard drive disk onto which data or displayed information obtained from the system is stored.

Another embodiment of the invention is directed to a system, further comprising software which performs a system integrity check. Another embodiment of the invention is directed to a system, wherein the system integrity check comprises calibration, verification of consistency of the software and the data, validation of algorithm software using a known calibration scheme, and verification of operation and functionality of the hard drive disk.

Another embodiment of the invention is directed to a system, wherein the broadband illuminator of the hyperspectral instrument head produces polarized visible light.

Another embodiment of the invention is directed to a system, wherein the system measures diffusely reflected backscattered light at 15 wavelengths between 500 and 660 nm. Another embodiment of the invention is directed to a system, wherein the backscattered light is measured at increments of 5 nm, 10 nm, 15 nm, 20 nm, 25 nm, 30 nm, 35 nm, 40 nm, or combinations thereof.

Another embodiment of the invention is directed to a system, further comprising a two-dimensional CMOS detector.

Another embodiment of the invention is directed to a system, further comprising a liquid crystal tunable filter.

Another embodiment of the invention is directed to a method for determining a tissue oxygenation measurement comprising: obtaining a hyperspectral/multispectral image of a tissue of interest; performing spectral analysis at each point in a two-dimensional scanned area, wherein the spectral analysis comprises determining approximate values of oxygen saturation, oxyhemoglobin levels, and deoxyhemoglobin levels in superficial tissues; and displaying tissue oxygenation in a two-dimensional, color-coded image.

Another embodiment of the invention is directed to a method, wherein the method takes less than 30 minutes, less than 15 minutes, less than 10 minutes, less than 5 minutes, or less than 2 minutes.

Another embodiment of the invention is directed to a method, wherein the tissue oxygenation measurement correlates with hemoglobin oxygen saturation in superficial capillaries of the tissue of interest.

Another embodiment of the invention is directed to a method, wherein the tissue is free of wounding or ulceration and is devoid of free, extravasated hemoglobin.

Another embodiment of the invention is directed to a method, comprising measuring diffusely reflected backscattered light at 15 wavelengths between 500 and 660 nm.

Another embodiment of the invention is directed to a method, wherein the 15 wavelengths are captured by sequentially tuning voltage on a liquid crystal tunable filter.

Another embodiment of the invention is directed to a method, wherein a patient with the tissue of interest has a skin temperature of between 30° C. and 35° C.

Another embodiment of the invention is directed to a method, wherein the spectral analysis further comprises recording light reflected from the tissue of interest at a specific wavelength into a hypercube array that holds a three-dimensional matrix of hyperspectral data.

Another embodiment of the invention is directed to a method, wherein the reflected light from the tissue of interest at a particular pixel is converted into absorption spectra by comparing the reflected light from the tissue to a background illumination signal using the following algorithm:

$$A_T(x, y, \lambda) = -\log_{10}\left(\frac{I_t(x, y, \lambda) - B'(x, y, \lambda)}{I_O(x, y, \lambda) - B'(x, y, \lambda)}\right),$$

wherein $I_t$ and $I_o$ are reflective intensities collected from the tissue; $B'$ is the background illumination signal recorded with a closed camera aperture; x and y are spatial dimensions for collected scans; $\lambda$ is the specific wavelength at which the reflected light from the tissue is recorded; and $A_T$ is the absorption spectrum of the tissue of interest.

Another embodiment of the invention is directed to a method, further comprising controlling for melanin contribution and diffuse scattering losses using the following equation:

$$A_H(\lambda,x,y) = A_T(\lambda,x,y) - (b_2(x,y)\lambda^2 + b_1(x,y)_2 b_0(x,y)),$$

wherein $b_0$, $b_1$ and $b_2$ are coefficients determined by minimizing the squared difference between the fit and data at 520, 530, 620, 640 and 660 nm, and $A_H$ is the absorption spectrum signal that remains attributed predominantly to hemoglobin absorption.

Another embodiment of the invention is directed to a method, further comprising calculating second fit to determine relative contributions of oxyhemoglobin and deoxyhemoglobin using the following equation:

$$\text{fit}(\lambda,x,y) = c_3(x,y) \times \text{deoxyHb}(\lambda) \times K(\lambda) + c_2(x,y) \times \text{oxyHb}(\lambda) \times K(\lambda) + c_1(x,y) \times K(\lambda) + c_0(x,y),$$

wherein $c_0$, $c_1$, $c_2$ and $c_3$ are coefficients determined by minimizing the squared difference between the fit and the recorded hyperspectral scan for wavelengths between 530 and 590 nm and $K(\lambda) = (\lambda - 500)/300$ as a correlation for melanin absorption.

Another embodiment of the invention is directed to a method, wherein the coefficients $c_2$ and $c_3$ are used to calculate percent hemoglobin oxygen saturation, $$HTSat(x, y) = \frac{c_2(x, y)}{c_2(x, y) + c_3(x, y)} \times 100\%.$$

Another embodiment of the invention is directed to a method, further comprising evaluating the relative contribution of oxyhemoglobin and deoxyhemoglobin to the tissue spectra, using the following equations:

$$HTOxy(x, y) = \frac{HTSat(x, y) \times HTTHb(x, y)}{100}$$

and $$HTDeoxy(x, y) = HTTHb(x, y) - oxyHb(x, y).$$

Another embodiment of the invention is directed to a method of displaying hyperspectral or multispectral imaging information of a tissue on a two-dimensional screen whereby medical information associated with areas of the tissue is displayed by placing a cursor over the area of interest.

Another embodiment of the invention is directed to a method, wherein the medical information is information pertaining to the oxygen status of the tissue area.

Another embodiment of the invention is directed to a system, wherein the display comprises Point and Click technology allowing a user to select any region of the scanned surface for which an average value of measurements of the selected region is displayed.

Another embodiment of the invention is directed to a system, wherein the measurements include any one or more of the group consisting of:
 a value for oxyhemoglobin;
 a value for deoxyhemoglobin;
 a value for percent oxygen saturation;
 automatic ulcer border mapping;
 semiautomatic ulcer border mapping;
 a value for ulcer size;
 a value for ulcer depth
 an ulcer healing index; and
 an ulcer prediction index.

Another embodiment of the invention is directed to a system, wherein the ulcer healing index comprises any one or more of the group consisting of:
 a comparison of one or more values inside the ulcer to one or more values outside the ulcer;
 a comparison of one or more values outside the ulcer to one or more values measured from a patient's other foot;
 a comparison of one or more values outside the ulcer to one or more values measured from the patient's forearm;
 a comparison of one or more values outside the ulcer to one or more values measured on a previous visit of the patient;
 a comparison of one or more values inside or outside the ulcer to one or more pieces of clinical data such as blood pressure or neuropathy measures; and
 a comparison of a response of one or more values inside or outside the ulcer to leg dependency, blood pressure cuff induced ischemia, exercise induced ischemia, or administered oxygen.

Another embodiment of the invention is directed to a system, wherein the ulcer prediction index comprises any one or more of the group consisting of:
 a comparison of one or more values from a site of interest to one or more values outside the site of interest;
 a comparison of one or more values outside the site of interest to one or more values measured from a patient's other foot;
 a comparison of one or more values outside the site of interest to one or more values measured from the forearm;
 a comparison of one or more values outside the site of interest to one or more values measured on a previous visit of the patient;
 a comparison of one or more values inside or outside the site of interest to one or more pieces of clinical data such as blood pressure or neuropathy measurements.
 a comparison of one or more values inside or outside the site of interest to leg dependency, blood pressure cuff induced ischemia, exercise induced ischemia, or administered oxygen.

Other embodiments and advantages of the invention are set forth in part in the description, which follows, and in part, may be obvious from this description, or may be learned from the practice of the invention.

DESCRIPTION OF THE FIGURES

FIG. 11 OxyVu-1 System Architectural Design Chart.

DESCRIPTION OF THE INVENTION

Device Description

Figure 1:
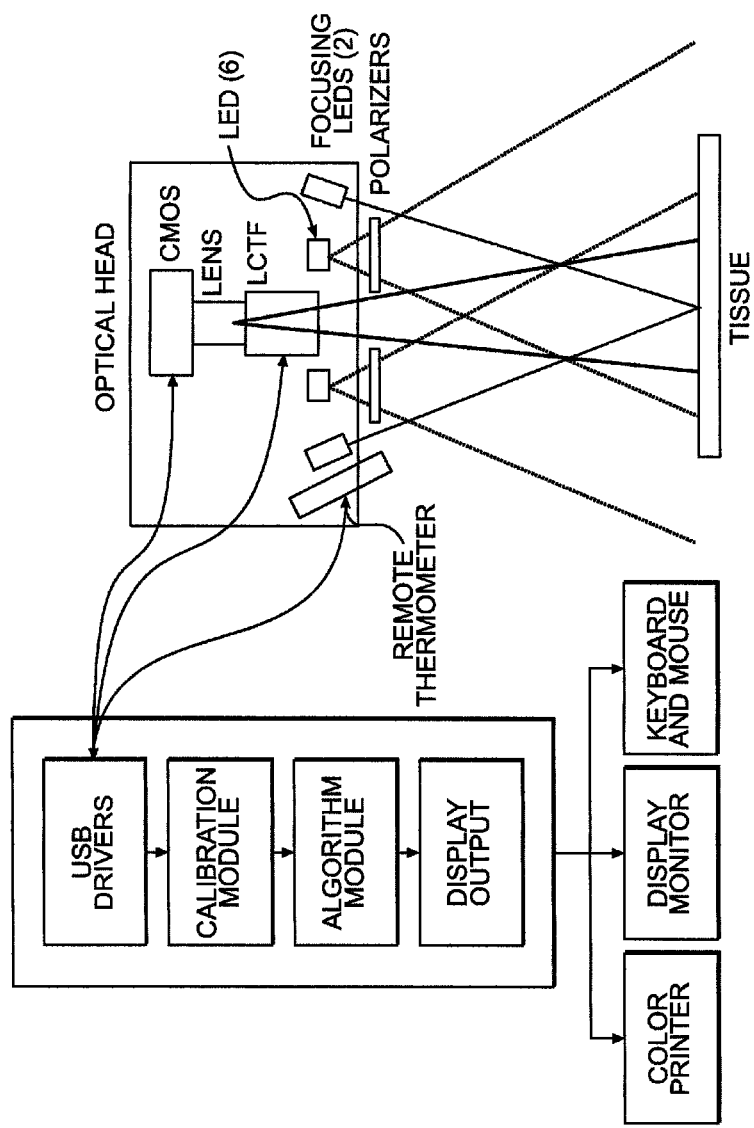
FIG. 1 Functional block diagram of the major OxyVu components.

As embodied and broadly described herein, the present invention is directed to a hyperspectral/multispectral system tentatively referred to as the OxyVu-1 system. The term OxyVu or OxyVu-1 (and OXYVU™) are intended to be a general reference to the general device and are not intended to represent specific embodiments. The hyperspectral imaging technology performs spectral analysis at each point in a two-dimensional scanned area producing an image displaying information derived from the analysis. For the OxyVu-1 system, the spectral analysis determines in superficial tissues approximate values of oxygen saturation (HT-Sat), oxyhemoglobin levels (HT-Oxy), and deoxyhemoglobin levels (HT-Deoxy). The OxyVu-1 system displays the tissue oxygenation in a two-dimensional, color-coded image.

The system contains a system console, a cart, system electronics, CPU, monitor, keyboard, pointing device and printer. The hyperspectral instrument head with support arm contains broadband illuminator, camera and spectral filter for collecting hyperspectral imaging cube. The single use OxyVu Check Pads and Targets are used to perform an instrument check prior to patient measurements. The OxyVu Target is placed within the intended field of view and is used as a fiduciary mark for image registration and for focusing.

Device Use

The OxyVu-1 Hyperspectral Tissue Oxygenation (HTO) Measurement System is intended for use by healthcare professionals as a non-invasive tissue oxygenation measurement system that reports an approximate value of: oxygen saturation (HT-Sat), oxyhemoglobin level (HT-Oxy), and deoxyhemoglobin (HT-Deoxy) level in superficial tissue. The OxyVu-1 system displays two-dimensional color-coded images of tissue oxygenation of the scanned surface and reports hyperspectral tissue oxygenation measurements for selected tissue regions.

The OxyVu-1 system determines oxygenation levels in superficial tissues for patients with potential circulatory compromise.

TABLE 1

Comparison with a Predicate Device

| | OxyVu-1 | Inspectra Model 325 |
|---|---|---|
| Measures | Oxygen saturation Oxyhemoglobin level Deoxyhemoglobin level | Oxygen saturation |
| Method of Measurement | Spectral analysis at specific wavelengths of light returned from target tissue. | |
| Output Display | Numeric Two-dimensional color map of approximate tissue oxygenation | Numeric |

Similarities and Differences

OXYVU™ is manufactured by HyperMed, Inc (Waltham, Mass.), and Inspectra™ Model 325 is manufactured by Hutchinson Technology (Hutchinson, Minn.). Both devices use spectral analysis to determine oxygenation levels in near-surface tissues. Both devices display numeric values of the approximate oxygen saturation of the hemoglobin. The OxyVu-1 system also displays the related approximate oxyhemoglobin and deoxyhemoglobin levels necessary for the oxygen saturation calculation.

The hyperspectral scanning method used by the OxyVu-1 system provides two-dimensional mapping of color-coded oxygenation levels. Based on equivalent intended uses and technologies and on comparable results in clinical testing, the OxyVu-1 Hyperspectral Tissue Oxygenation Measurement System is substantially equivalent to the Inspectra Model 325 Tissue Spectrometer System.

OxyVu-1 is the only device that provides a tissue oxygenation scan with a 100 micron resolution. Resolution can be decreased or increased as desired such as, for example, 50 micron or 150 micron, 25 or 200 micron, 25 or 300 microns, or more.

Tissue oxygenation information can be viewed pixel-by-pixel, as a region of interest, or for an entire region. Given the heterogeneity of tissue, this provides a substantial improvement over existing point spectroscopy methods.

OxyVu-1 provides quantitative measurements for every pixel of the scan. These measurements indicate levels of oxy-hemoglobin and deoxy-hemoglobin, indicating both the oxygen "supply" and oxygen "demand" characteristics of the tissue.

A complete OxyVu-1 exam takes less than 30 minutes, typically less than 15 minutes, preferably less than 10 minutes and more preferably less than 5 minutes. This is one quarter the time currently required for a $TcPO_2$ exam, and yet the OxyVu-1 exam provides more quantitative data. Some of the advantages include the facts that: no warm up time is necessary; measurements are taken in under 20 seconds per site, preferably under 10 or 15 seconds, more preferably under 5 seconds or more preferably within 2 seconds; OxyVu-1 does not contact the patient; the OxyVu-1 reports measurements in a user-friendly format; measurements at the beginning and end of a therapy session can be compared; and measurements from different visits can be compared. For example, OxyVu-1 measurements reflect oxygenation physiology in the region near a wound or ulcer. The operator just positions the OxyVu-1 sensor over the tissue to be measured and then initiates the calibration and measurement cycle. OxyVu-1 does the rest. The OxyVu-1 Hyperspectral Tissue Oxygenation (HTO) Measurement System provides noninvasive measurement of tissue oxygenation, sensitive to local, regional and systemic low/no-flow ischemia.

The OxyVu-1 HTO Measurement System comprises a durable, reusable OxyVu-1 Instrument; and disposable calibration OxyVu Check Pads and Targets. OxyVu-1 instrument calibration is assured when scanning with the OxyVu Check Pad prior to each patient study. Correction for patient motion is assured when also included is an OxyVu Target in each image collected.

Principle of Operation

Hemoglobin in its various forms (oxyhemoglobin and deoxyhemoglobin) has unique spectroscopic properties that allow tissue oxygen saturation and levels of the hemoglobin forms to be determined by measuring spectral characteristics. The OxyVu-1 uses broadband, multi-wavelength illumination, and hyperspectral analysis to determine estimated values of tissue oxygenation measurements including hyperspectral tissue oxyhemoglobin levels (HT-Oxy), deoxyhemoglobin levels (HT-DeOxy), and the calculated oxygen saturation (HT-Sat). Hyperspectral analysis provides a two-dimensional map from which tissue oxygenation measurements from a defined or user-selected region can be selected.

OxyVu-1 Display

The OxyVu-1 display contains a color bar which indicates the color coding for the HT-Oxy and HT Deoxy levels in the scan. If no region is selected, the numerical display represents the average values for the four centimeter square around the target. If the user selects a different region, the numerical display represents the average values for the selected region, which may be a donut or pre-selected area. These tissue oxygenation measurements are displayed:

HT-Sat: an approximate measure of the oxygen saturation of hemoglobin

HT-Oxy: an approximate measure of the oxyhemoglobin level

HT-Deoxy: an approximate measure of the deoxyhemoglobin level

Understanding OxyVu-1 Readings

Capillary-Weighted

Hemoglobin oxygen saturation of blood in superficial microvascular tissue is typically lower than arterial saturation ($SaO_2$) and can be lower than central venous saturation ($SvO_2$), which represents a mix from blood returning from many tissues. Hyperspectral tissue oxygenation measurements correlate with the hemoglobin oxygen saturation in superficial capillaries of the scanned tissue. Tissue oxygenation measurements are affected by changes in arterial oxygenation and by changes in blood flow (low/no-flow ischemia). Normal tissue saturation (HT-Sat) ranges have been established as described in Table 2.

TABLE 2

Normal Ranges of Oxygenation Values for arterial sampling, pulse oximetry, TcPO$_2$ andOxyVu tissue oximetry.

| Value | Normal Range | Description |
|---|---|---|
| SaO$_2$(or SpO$_2$) | 95-100% | Arterial hemoglobin saturation. Commonly estimated by Pulse Oximetry |
| TcPO$_2$ | 49-67 torr (or mm Hg) | Partial Pressure of free diffusing oxygen in skin |
| OxyVu-1 HTO: | | Tissue hyperspectral oxygenation measurements reflecting oxygen delivery and oxygen extraction in superficial capillary beds. |
| HT-Sat | 23-46% | |
| HT-Oxy | 23-54% | |
| HT-Deoxy | 59-105% | |

Normal HTO measurement ranges values for tissues other than skin have not yet been established, but can be determined by one or ordinary skill in the art using the devices, methods and analysis of the invention.

Sensitive to Low/No Flow Ischemia

Reduced blood flow ischemia states are detected by hyperspectral tissue oxygenation measurements (HT-Sat, HT-Oxy, HT-Deoxy). During reduced blood flow ischemia (such as from arterial occlusion, microvascular disease, thrombosis, shock or cardiac failure), the arterial saturation may remain unchanged, but the reduced blood flow results in lowered tissue oxygenation measurements due to a high fractional extraction of delivered oxygen to the capillaries.

Hyperspectral tissue oxygenation, which is measured in superficial capillaries, differs from arterial oxygenation as measured by pulse oximetry. Hyperspectral tissue oxygenation measurements are influenced by arterial blood oxygenation (SaO$_2$%), as well as by blood flow and blood hemoglobin content.

Measured values are affected by blood in direct contact with air. Care should be taken to ensure the portion of the surface chosen for measurement is outside of any area of wounding or ulceration and is devoid of free, extravasated hemoglobin. While measurements may be obtained within wounded or ulcerated tissue, reference ranges have not yet been established.

With its non-contact technology, OxyVu-1 does not have artifacts associated with pressure seen with probe based technologies.

OxyVu Check Pads and Targets are preferably designed for single use only, but may also be designed for multiple applications. Reuse may affect calibration and interfere with instrument operation.

Monitoring Oxygenation

To use the OxyVu-1 system, place the cart two meters or less from the patient. The test environment should provide comfortable patient positioning, preferably supine or a chair with leg elevation. Room temperature should be preferably in the range of 72° F. to 80° Fahrenheit (22° C. to 27° Celsius). Nevertheless, due to the methods and processes of the invention, room temperature can be most any number (or range) and the calculations made and corrected accordingly. Other room temperatures include from 15° C. to 20° C., from 20° C. to 25° C., from 25° C. to 30° C., or from 30° C. to 40° C. Preferably, ambient lighting should not include extremely bright or fluorescent light.

Detailed Technician Procedure

1. Bring the patient into the examination room.
2. Remove the patient's shoes, socks, and bandage materials, if any.
3. Inspect the area to be scanned and clean if necessary.
4. Have the patient lie supine on the examining table or sit in the examination chair.
5. Roll up the shirt sleeve to expose one forearm and the legs of pants to expose each calf.
6. Enter patient identification data.
7. Open the OxyVu Calibration Pack and remove the OxyVu Check Pad.
8. Place the OxyVu Check Pad in its holder and position the hyperspectral instrument head 18 inches from the OxyVu Check Pad.
9. Turn on the focus lights and verify that they come together to form a single circle on the check pad.
10. Turn off the focus lights.
11. Take a measurement from the OxyVu Check Pad to ensure appropriate calibration, focus and correction for background lighting.
12. Remove an OxyVu Target (7 mm pad with hydrogel backing) from the OxyVu Calibration Pack and place it on the patient's first site to be studied, for example, the forearm.
13. Position the arm comfortably at the patient's side to minimize motion during the study.
14. Place the hyperspectral instrument head 17 inches the patient's arm and turn on the focusing lights. Adjust the instrument head until the focusing beams converge on the target. Turn off the focusing lights.
15. Initiate a measurement scan. A measurement can be set to acquire over a 15 second period.
16. Check the screen to confirm an adequate measurement. The processed spectral data is displayed on a computer screen along with numerical HTO measurements (HT-Oxy, HT-Deoxy and HT-Sat) averaged over the central portion of the scanned site.
17. When appropriate, select specific region(s) of interest within the scan from which to obtain additional quantitative HTO measurements (for example, near an ulcer).
18. The OxyVu-1 system records the quantitative oxygenation measurements for the measured sites along with data display of the tissue map.
19. Repeat the steps above for additional sites.
20. Print out data from all sites Detailed Physician Procedure 1. Obtain a print out of the HTO measurements.
2. Review and interpret the hyperspectral scan and the numerical measurement for each site.
3. Review specific regions of interest chosen by the technician.
4. If appropriate, access stored hyperspectral data from previous examinations further review.
5. If on review, you want to obtain numerical measurements from other regions of interest, do so by recalling the stored hyperspectral data. Now select other region(s) of interest for measurement.
6. Compare new HTO data from one or more sites or specific regions of interest with HTO data taken during any previous examinations.
8. Consider the HTO data from all sites and regions of interest and put the HTO data into context with other clinical and laboratory information to complete the clinical interpretation.
9. Saving Data to Internal Disk The successfully acquired data and final color-coded image are automatically saved onto the hard drive disk. These can be retrieved for additional examination, a follow-up study for a comparison, or for later printing. The software checks the volume of free space on the hard drive. It prompts the user when the hard drive is 90% full. The system then suggests to store the older data on an optical storage device (e.g. CD or DVD) and delete these data from the hard drive.

Data File Naming Convention

All hypercube data acquired for a particular subject on the date of measurements, as well as system status files are automatically stored in a directory named "data", into a subdirectory named as follows: "YYYYMMDDsubjectID".

The files are automatically named using the subject ID, the observed site name, and the date and time of the acquisition, as follows: subject_site_YYYYMMDDTHHMMSS.mat For example, hyperspectral data recorded off left dorsum of a subject with ID: CC03451 on May 21, 2006 at 2:34:17 pm would be saved under the name: CC03451_1_dorsum 20060521T143417.mat In addition to the data files, the OxyVu Check Pad data are stored in the same directory with the name as follows: subject_pad_YYYYMMDDTHHMMSS.mat (In the example above, it would be: CC03451_pad_20060521T140407.mat—note that the OxyVu Check Pad data were acquired 30 minutes prior to dorsum data).

The state of the system is recorded into an exit file upon completion of subject measurements, with the name as follows: subject_exit_YYYYMMDDTHHMMSS.mat The resulting pseudo-color image is stored into a file of a graphical format, for example: subject_site_YYYYMMDDTHHMMSS.jpg
File Folders OxyVu-1 files are grouped into subfolders in a Data Folder.
Data Files OxyVu-1 produces 3 types of output files in Windows PC format:

| | |
|---|---|
| Data File: | Save As: Binary File (*.mat) |
| Results File | Save As: graphical files (*.jpg) |
| Note/Log File | Save As: ascii text files (*.txt) |

File Format:

For export, the result data files are saved as graphical files, and can be opened using any graphical program running on any computer system. The note/log files are saved as ascii text files and can be opened using any text reading program on any computer system.

Moving Stored Data

When data are stored (see above), they are saved to the internal OxyVu-1 Oximeter hard drive. Stored data can be transferred to a ZIP™ or other USB Storage device as follows:
1. Connect storage device to the USB data port (on rear panel of monitor).
2. From the main screen, select Options.
3. Select Manage Files. There is a brief pause before data copying status is displayed.
4. Wait until copying is done and "Copy Complete" is displayed before removing the disk. Press Done to complete. If the disk becomes full, copying will stop and a message is displayed describing the number of files copied and the number remaining to be copied. The remaining files can be copied by inserting another memory device and repeating the steps above.

Changing Date and Time
1. From the main screen, press Options.
2. Press Set Clock.
3. Use the up/down arrows to change the time, date and time units (12 h vs. 24 h, AM or PM).
4. Press Accept Change or Discard Changes to finish.
5. Checking Software Version Numbers Software versions and the results of a system integrity check using the Versions screen may be viewed as follows:
1. From the main screen, select Options.
2. Press Versions.
3. When finished viewing, press Options Done.
Self-Test and Errors The OxyVu-1 system performs a self-test upon power-up. With calibration, additional testing is performed including a verification of consistency of the program software and support files, validation of the algorithm software using a known calibration scheme, and operation and functionality of the hardware.

Fundamental Principles of Operation

The OxyVu-1 Hyperspectral Tissue Oxygenation (HTO) Measurement System shares fundamental principles with other oximeters and tissue oxygenation measurement systems. Oxyhemoglobin (oxyHb) and deoxyhemoglobin (deoxyHb) levels are determined using spectral analysis at specific wavelengths. Oxygenation saturation (SO2) is calculated:

$$SO2 = oxyHb/(oxyHb + deoxyHb) \times 100\%$$

Tissue oximetry devices expose tissue with radiation of known wavelengths and measure the returned light. Wavelengths are chosen that provide hemoglobin information at intended tissue locations. 1-8 Wavelengths chosen for the OxyVu-1 provide information in the superficial capillary spaces.

The OxyVu-1 source illumination is broadband visible light, polarized to avoid specular reflection (surface glare). The OxyVu-1 preferably measures diffusely reflected back-scattered light at 15 wavelengths between 500 and 660 nm using a 2-dimensional CMOS detector and a liquid crystal tunable filter as a spectral separator. Measurements may include additional wavelengths above and within this range such as, for example, from 400 to 700 nm, preferably from 280 to 600 nm, or from 350 to 550 nm, or from 450 to 800 nm, or from 400 to 500 nm and 550 to 650 nm, or combinations thereof and therein. Increments may be selected at 5, 10, 15, 20, 25, 30 or 35 nm, or even greater lengths or at useful combinations thereof.

Hyperspectral analysis produces a two-dimensional (2-D) array of tissue oxygenation measurements by making a set of measurements at each pixel. If each set of measurements is considered a third dimension, the OxyVu-1 system collects a 3-D matrix of spectral measurements. The OxyVu-1 2-D array has 0.1 mm spatial resolution within a 10 cm×13 cm field of view. As is clear to those skilled in the art, the field of view may be nearly any field that encompasses the area of interest and provides a view of the tissue of interest. Field of view is typically empirically determined. From this array, any region of interest chosen can be queried, and a hemoglobin oxygen saturation (HT-Sat) measurement can be derived for the region. The HT-Sat measurement reflects the average oxygen saturation for the region. Averaging multiple data points minimizes error due to inherent tissue heterogeneity. (Note: Unlike pulse oximeters, OxyVu-1 measurements need not be synchronized to the arterial pulse because the OxyVu-1 measures hemoglobin oxygen saturation from superficial tissue (within ~1 mm). The majority of the return signal corresponds to the sampling of hemoglobin in the dermal capillary bed.)

Functional Block Diagram

The block diagram shown in FIG. 1 depicts the major OxyVu-1 functional components including the subcomponents within the optical head. The computer console houses the USB drivers and software modules which interface with the operator via a monitor, keyboard and mouse. The optical head includes a toggle switch for switching between the focusing lights and the white light illumination lights (LEDs). The optical head and supporting electrical connections are connected to the console by way of an articulating arm. The operator would first calibrate the system by taking an image of the OxyVu Check Pad following instructions on the computer monitor. The operator would then focus and align the optical head onto the tissue surface by positioning the optical head such that the two spots from the focusing lights overlap and are positioned in the center of the field of view. An OxyVu Target would also be place onto the skin surface within the field of view. The bottom surface of the optical head would also be adjusted to be parallel to the tissue surface. The operator would then switch off the focusing lights and turn on the illumination lights to collect hyperspectral images from the tissue site of interest.

For each site, images are captured at 15 wavelengths by sequentially tuning the voltage on the liquid crystal tunable filter and focusing the surface onto a CMOS detector. Nevertheless, it is within the skill of the user to operate with more or less than 15 wavelengths such as, for example, 5 wavelengths, 10 wavelengths, 20 wavelengths, 25 wavelengths or more. Image data are passed back to the console via USB drivers and processed through the calibration module, algorithm module and output display module as shown in FIG. 1.

Hyper-Spectral Solution Output Display

Figure 2:
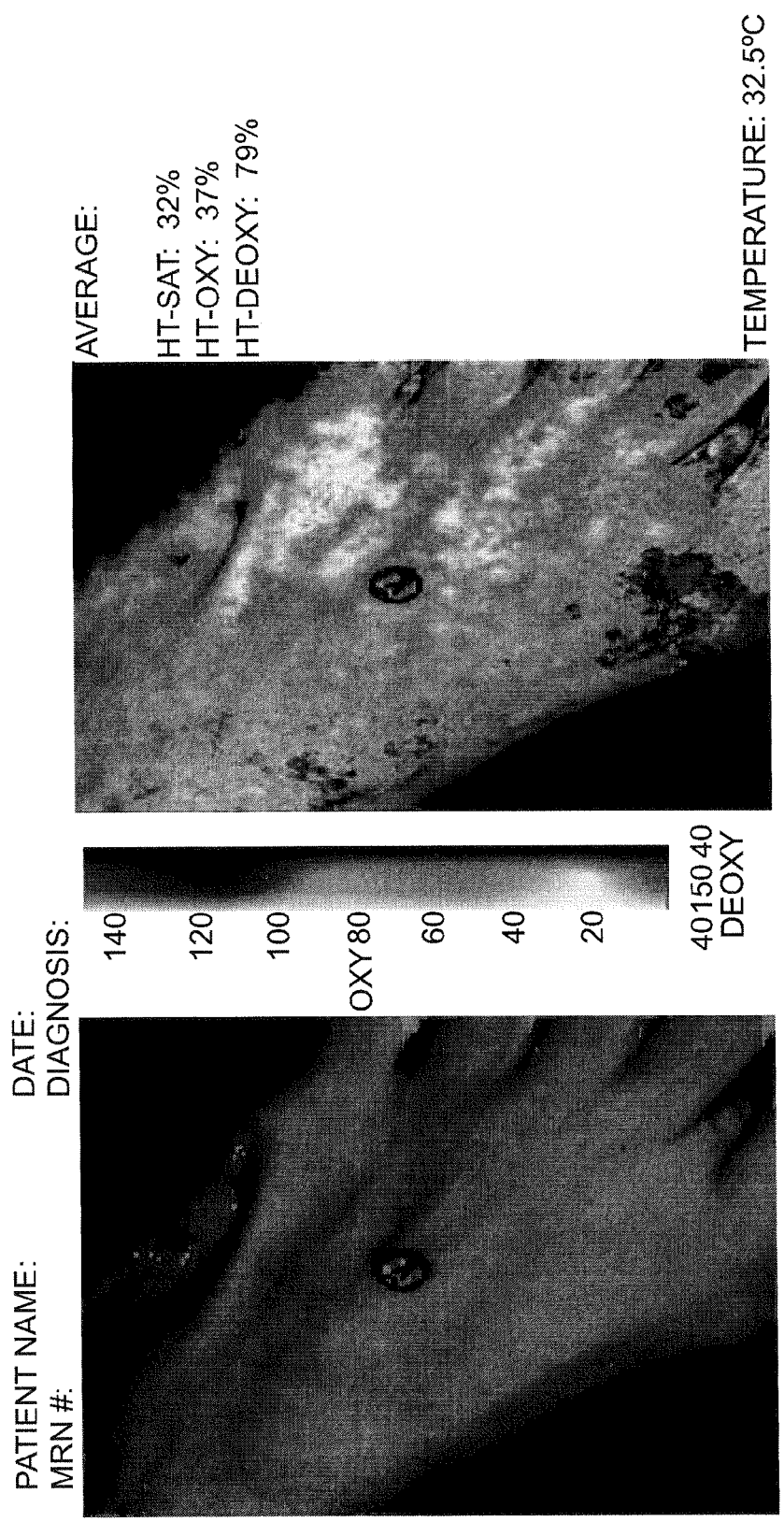
FIG. 2 OxyVu-1 Display.

A pseudo-color map is created as a way to present tissue oxygenation status to the end user in an image format. Starting in HSV color coordinates (hue, saturation, value), the apparent concentration of oxyHb is mapped to the color hue plane, the apparent concentration of deoxyHb is mapped to the color saturation plane, and the intensity of the diffuse reflectance of the tissue preferably at 570 nm is mapped to the value plane. Intensity may also be mapped at 425 nm, 450 nm, 475 nm, 500 nm, 525 nm, 550 nm, 575 nm, 600 nm, 625 nm, 650 nm, or higher, which may vary by 5, 10 or 15 nm as determined by the user. The hyperspectral solution is obtained from a hyper-cube that is smoothed by binning four pixels in the spatial dimension. To preserve the high resolution of the system, the apparent concentration of oxygenated Hb, or deoxygenated Hb, are preferably interpolated onto the original grid of the value plane. Therefore, the spatial resolution of the pseudo-color display remains unchanged. The HSV display is then mapped to a RGB display. The hyperspectral map is then displayed to the end user. The average values for oxyHb, deoxyHb and oxygen saturation from a region of interest selected by an end user is displayed on the output display. The patient's name and medical record number and date of the visit is also part of the display output. An example of the output display is shown in FIG. 2.

Algorithm

The OxyVu-1 system collects a 3-D matrix of data during each scan. For each pixel in the two-dimensional scan, the system records the light reflected from the skin at specific wavelengths. This "hypercube" array of data holds the hyperspectral data. To analyze the hyperspectral data, the reflected light from the tissue at each pixel is first converted into absorption spectra by comparing to the reflected illumination signal using the following method:

$$A_T(x, y, \lambda) = -\log_{10}\left(\frac{I_t(x, y, \lambda) - B'(x, y, \lambda)}{I_0(x, y, \lambda) - B'(x, y, \lambda)}\right)$$

Figure 3A:
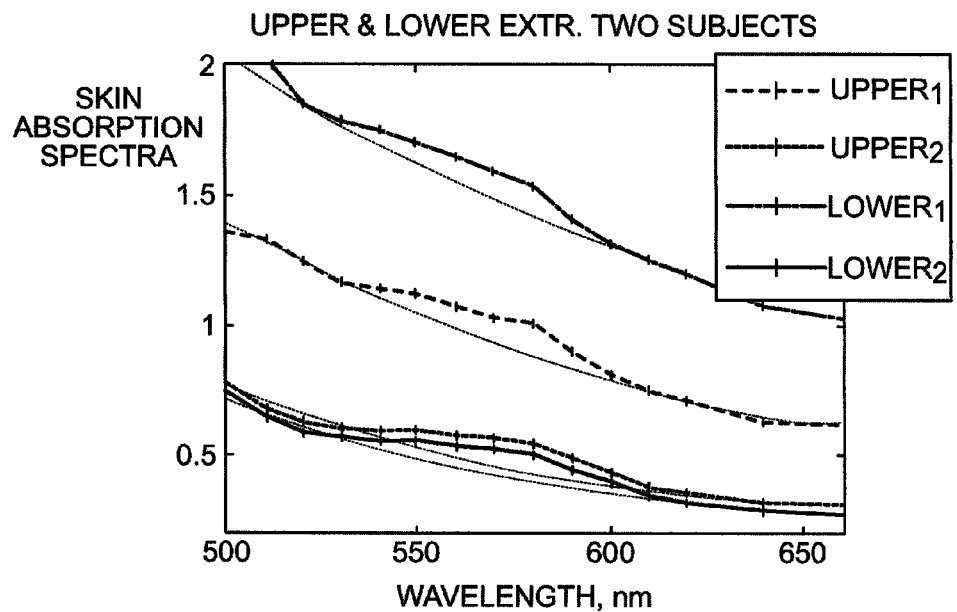
FIG. 3(a) Typical skin absorption spectra recorded from a darker skin subject (red and blue lines) and a lighter skin subject (green and cyan lines). Two sites for each subject are shown: upper extremity (blue and green) and lower extremity (red and cyan).

The terms $I_t$ and $I_o$ are the reflectance intensities collected from tissue (or the flat white diffusely reflective portion of the OxyVu Check Pad.). The background signal, B', is recorded with the aperture closed on the camera. The spatial dimensions for the collected scans are denoted with x and y. An example of the resulting absorption spectra is shown in FIG. 3(a), solid lines with dots. Typical skin absorption spectra recorded from a darker skin subject and a lighter skin subject. Two sites for each subject are shown: upper extremity and lower extremity.

The residual spectra from FIG. 3, panel a, the observed spectra minus background due to melanin and diffuse scattering, reflect absorption due to hemoglobin in the skin. The first step in the analysis is to evaluate contribution from the melanin and the scattering effects of skin. The darker skin absorbs more light, therefore their spectra show higher values. These are modeled as a polynomial of second degree (dotted lines) and removed from the observed spectra. Relative contribution to residual spectra is shown in FIG. 3(c). The contribution from diffuse scattering is shown by the dotted line. Once deoxyHb contribution is added, the 3-component contribution is shown by solid crossed line. Similarly, the 3-component contribution (offset, slope, and oxyHb) is shown by the solid line with circles. FIG. 3(d) is an example of fit and the residual spectra is shown. The quality of fit is achieved by minimizing the squared difference between the fit and the data. Coefficients for oxyHb and deoxyHb are obtained to calculate the HT-Sat oxygen saturation of the skin. The values for HT-Sat for both subjects at two sites are determined.

The spectrum at each pixel location resembles an absorption spectrum of a mixture of oxyHb and deoxyHb, displaced by a background that is predominantly attributed to melanin absorption and light loss due to scattering outside the collection cone of the detector. A second order polynomial is used to subtract the contribution from melanin and diffuse scattering losses (see FIG. 3(a) dotted lines):

$$A_H(\lambda,x,y) = A_T(\lambda,x,y) - (b_2(x,y)\lambda^2 + b_1(x,y)\lambda + b_0(x,y)) \quad \text{(Eq. 2)}$$

The coefficients b0, b1 and b2 are determined by minimizing the squared difference between the fit and data at 520, 530, 620, 640 and 660 nm. Representative spectra for $A_H(\lambda, x,y)$ are shown in FIG. 3(b).

Figure 3B:
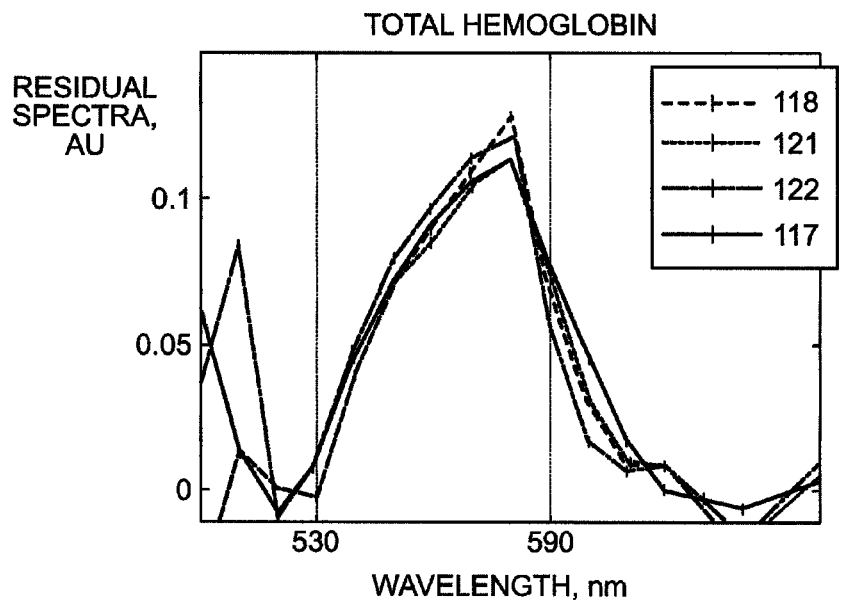
FIG. 3(b) The residual spectra from panel a, the observed spectra minus background due to melanin and diffuse scattering, reflect absorption due to hemoglobin in the skin.
Figure 3C:
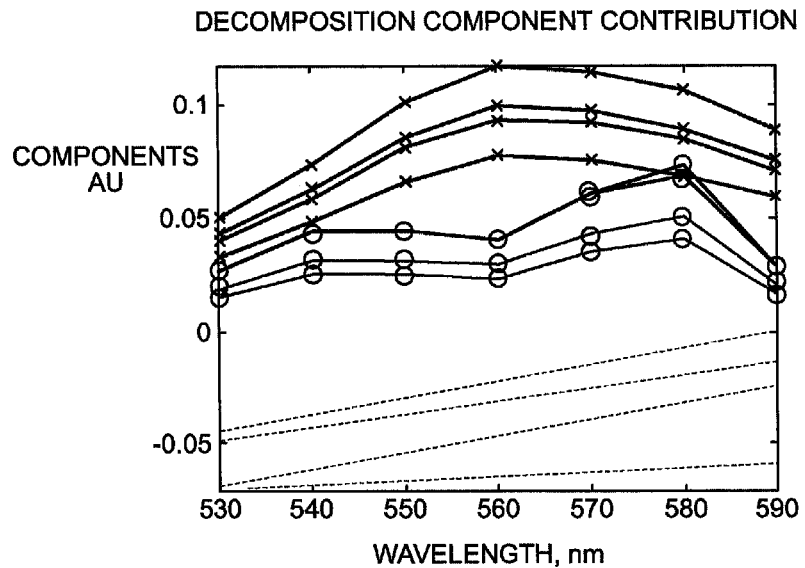
FIG. 3(c) Relative contribution to residual spectra from diffuse scattering is shown by the dotted line. Once deoxyHb contribution is added, the 3-component contribution is shown by solid crossed line. Similarly, the 3-component contribution (offset, slope, and oxyHb) is shown by the solid line with circles.

The signal that remains is attributed predominantly to hemoglobin absorption (FIG. 3(b)). Therefore, the second step in the analysis is to calculate total hemoglobin (HT-THb) level in tissue by finding the area under the curve in the wavelength region between 530 and 590 nm. As an example, the value for HT-THb is given for FIG. 3(b) for both subjects and both sites. Once the HT-THb is evaluated, residual spectra are analyzed in the defined region. It can be assumed that four spectral components contribute to the shape and amplitude of the residual spectra in FIG. 3(b): two represent residual scatter (offset and slope), and other two are terms for deoxygenated and oxygenated hemoglobin. A linear decomposition is used to obtain the relative contribution for each component. An example of relative contribution is shown in FIG. 3(c). Therefore, the third step is to calculate second fit that is used determine the relative contributions of oxyHb and deoxyHb:

$$\text{fit}(\lambda,x,y) = c_3(x,y) \times \text{deoxyHb}(\lambda) \times K(\lambda) + c_2(x,y) \times \text{oxyHb}(\lambda) \times K(\lambda) + c_1(x,y) \times K(\lambda) + c_0(x,y) \quad \text{(Eq. 3)}$$

where the coefficients $c_0$, $c_1$, $c_2$, and $c_3$ are determined by minimizing the squared difference between the fit and the recorded hyperspectral scan for wavelengths between 530 and 590 nm and $K(\lambda)=(A-500)/300$ as a correction for melanin absorption. The absorption spectra for oxyhemoglobin (oxyHb) and deoxyhemoglobin (deoxyHb) are used as previously reported. The coefficients $c_2$ and $c_3$ are used to calculate the percent hemoglobin oxygen saturation, $$HTSat(x, y) = \frac{c_2(x, y)}{c_2(x, y) + c_3(x, y)} \times 100\%.$$

Figure 3D:
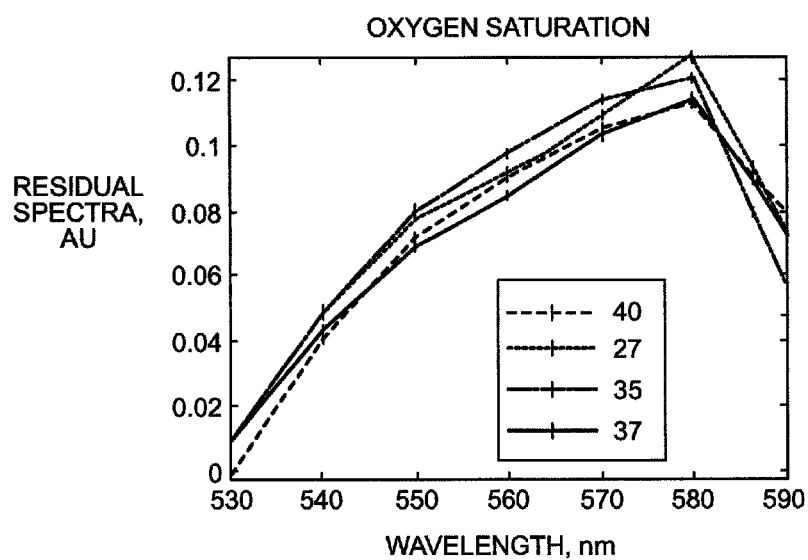
FIG. 3(d) An example of fit and the residual spectra.

Finally, the forth step in the analysis is to evaluate the relative contribution of oxyHb (HT-Oxy) and deoxyHb (HT-Deoxy) to the tissue spectra is then calculated using (see FIG. 3(d)):

$$HTOxy(x, y) = \frac{HTSat(x, y) \times HTTHb(x, y)}{100} \quad \text{(Eq. 5)}$$

and $$HTDeoxy(x, y) = HTTHb(x, y) - oxyHb(x, y). \quad \text{(Eq. 6)}$$

HT-Oxy and HT-Deoxy are proportional to the concentration of oxyHb and deoxyHb respectively. The penetration depth of the visible illumination light used by the OxyVu-1 (500 nm to 660 nm) is about or less than 1 mm (e.g. 0.1 mm, 0.2 mm, 0.3 mm, 0.4 mm, 0.5 mm, 0.6 mm, 0.7 mm, 0.8 mm, 0.9 mm, 1.0 mm). Increased intensity can increase penetration as can manipulation of the tissue surface or application of a penetrating agent such as a refractive oil or other transparent or relatively transparent composition. Penetration can be increased to 1.1 mm, 1.2 mm, 1.3 mm, 1.4 mm, 1.5 mm, 1.6 mm, 1.7 mm, 1.8 mm, 1.9 mm and 2.0 mm or more. Therefore, HT-Oxy and HT-Deoxy represent relative levels of oxy- and deoxy-hemoglobin measured in immediate small subsurface tissue volumes, and HT-Sat represents their mathematical combination. Spectra from the central four square centimeters of tissue sampled (that represent nearly 5,000 pixels) were averaged to provide tissue measurements of HT-Oxy, HT-Deoxy, and HT-Sat. The user may select another region from the 2-D scan.

Calibration

The basic concept of calibration is to confirm that the OxyVu-1 is measuring reflected light correctly. The software algorithm is based on published spectral properties of hemoglobin. Design validation confirms that given correct light measurements, the algorithm provides appropriate oxygenation measurements.

OxyVu-1 system calibration and checks are performed at four levels: Factory Calibration, Installation and Service Visit, Pre-Patient Checks, and Intra-Scan Checks. Calibration files created and stored during factory calibration or service visits are used during pre-patient calibration and to monitor the illumination source, the detector, and the collection optics to ensure that the system has not been damaged and to make sure the system is still functioning within specification since factory release or the last service visit.

Factory Calibration

The instrument is calibrated against known standards and a set of calibration files is stored on the system for use in evaluating the quality of the system during field testing and during calibration prior to each patient examination. The calibration files have information describing a baseline snapshot of the system after it has been aligned and calibrated. The technician undertakes the following steps during factory calibration:

Measures the output of the illumination source at the target with a power meter.

Verifies the wavelength filtering accuracy of the spectral separator by inputting light at three different wavelength within the operating range (e.g. 500, 550, and 650 nm) from a NIST traceable spectrometer filtered lamp.

Sets the gain and adjusts the offset to maximize the dynamic range of the detector.

Characterizes the dark noise and records dark signal at both minimal and maximal integration times.

Builds a sensitivity curve between 500 and 660 nm for diffuse reflectance measurements using a NIST traceable >99% diffuse reflectance imaging standard.

Builds an intensity/exposure time Look-Up Table by measuring the intensity at different camera exposure times while measuring the NIST traceable >99% diffuse reflectance imaging standard.

Verifies the characteristics of the system in the normal operating range by measuring diffuse reflectance against ~10%, ~30%, and ~50% NIST traceable reflectance standards over the spectral operating range.

Performs a final check of the system by recording a "full set" of spectra at 5 nm steps for the entire operating range of the spectral separator (~450 to 720 nm) from the NIST traceable >99% diffuse reflectance imaging standard. total integration time and spectral response for each wavelength are stored.

Once the instrument is calibrated, the technician performs a second "full scan", this time using an Oxy-Vu Check Pad so that measurements can be compared with the "full set" of data obtained from the reflectance standard and OxyVu Check Pad measurements stored in a file within the instrument to be recalled during service visits and pre-patient checks for comparison purposes. This checks for continued instrument performance within specifications. The following parameters are recorded Spectrum as recorded from the white central region of the Check Pad Spatial distribution of the detected signal as measured from the central region of the Check Pad Spectra as recorded from the two color bars of the Check Pad Focusing as determined by contrast assessment of barcode elements of the Check Pad.

Installation or Service Visit

A scan is taken of the OxyVu Check Pad and the OxyVu-1 system compares the scan data to values stored at Factory Calibration. The technician undertakes the following steps during installation or a service visit:

Scans the Oxy-Vu Check Pad to ensure that measured values for the four parameters describe above match data stored at factory calibration within defined tolerances.

If all parameters are found to be within defined tolerances then no alignments are needed.

If any parameter is found to be outside defined tolerance, then on-site or factory re-alignment and re-calibration is required.

Pre-Patient Checks

The pre-patient calibration procedure is designed to be simple. During pre-patient calibration, the operator records a single hyperspectral scan from the OxyVu Check Pad. Using this scan, the instrument compares scanned data to data stored in calibration files regarding each of the four parameters described above. If within operating tolerance, the system records ambient lighting conditions, and prompts the user to proceed to patient measurements.

If the OxyVu-1 determines that ambient light is too bright or has the spectral characteristics of fluorescent light, the operator is instructed to adjust the ambient light and repeat the measurement.

The pre-patient check measurement taken from Check Pad is stored and used as a reference for each measurement taken during a given patient measurement session If any parameter is found to be outside operating tolerance, the system prompts the user to assure compliance with recommended procedure and to repeat the Check Pad measurement. If the test results continue to fall outside operating tolerance, the operator is instructed in the user manual to call for service.

Intra-Scan Checks

The operator places an adhesive OxyVu Target on the tissue near the center of each region of interest to be scanned. The instrument performs the following additional checks during the acquisition of each measurement:

Identifies the OxyVu Target on the tissue surface

Measures and checks sharpness of OxyVu Target fiduciary markings to ensure that the focus is within operating tolerance Provides a check for patient motion that could compromise measurement quality Measures the features of the OxyVu Target to check that lighting conditions are not markedly different from those recorded during the pre-patient check A hyperspectral measurement of the OxyVu Check Pad is captured during factory calibration, service visits and pre-patient calibration procedures. Preferably, the OxyVu Check Pad is designed to have specific areas intended for specific system checks. The central area is a uniform white region used to characterize and test spectral and spatial parameters (described under Factory Calibration) and to provide a background reference for patient measurements. The red and blue color bars are used to assess spectral separator function (FIG. 4(a)). The barcode is used to both test focusing (FIG. 4(a)) and to ensure single use of the Check Pad to minimize the potential for using a soiled calibrator which could lead to inaccurate data collection.

Figure 4A:
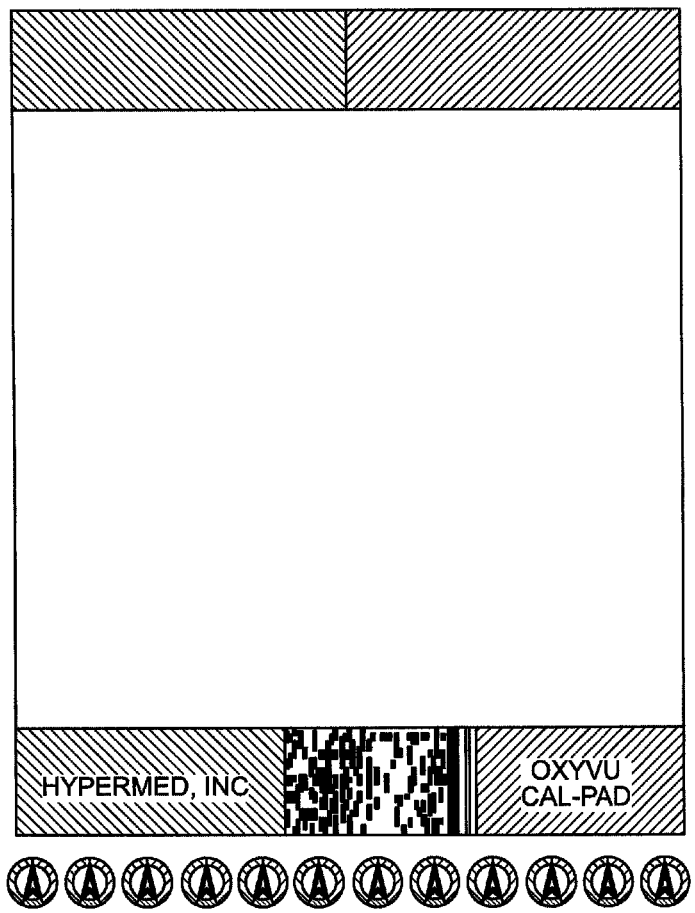
FIG. 4(a) OxyVu Calibration Pack showing OxyVu Check Pad and twelve OxyVu Targets.
Figure 4B:
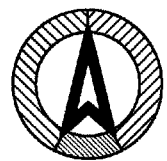
FIG. 4(b) OxyVu Registration Target.

The OxyVu Target (FIGS. 4(a) and (b)) is designed to perform checks during individual patient measurements. A single target is placed within the field of view of the OxyVu-1 System. The black arrowhead and other target features are used as a fiduciary mark to co-register the 15 spectral scans. The features of the OxyVu Target are also used to check that lighting conditions are not markedly different from those recorded during the pre-patient check.

Substantial Equivalence Comparison and Clinical Testing

Both devices, the OxyVu-1 and the Inspectra Model 325, use spectral analysis to determine oxygenation levels in near-surface tissues. Both devices display numeric values of the approximate oxygen saturation of the hemoglobin. The OxyVu-1 also displays the related approximate oxyhemoglobin and deoxyhemoglobin levels.

TABLE 3

Comparison to the Predicate Device

| | OxyVu-1 | Inspectra Model 325 |
|---|---|---|
| Measures | Oxygen saturation<br>Oxyhemoglobin level<br>Deoxyhemoglobin level | Oxygen saturation |
| Method of Measurement | LEDS illuminate the skin surface.<br>Spectral analysis at specific wavelengths of light returned from target tissue. | |
| | Fifteen wavelengths between 500 and 660 nm. | Four wavelengths between 680 and 800 nm. |
| | Uses a wavelength filtered CCD as the detector. | Uses 4 wavelength filters photomultiplier tubes. |
| | Uses oxyHb and deoxyHb spectra and a slope and offset to fit the measured tissue spectra. Oxygen saturation is calculated from the oxyHb and deoxyHb fit coefficients. | Uses a 40-nm wide second derivative method to determine oxygen saturation using the diffuse reflectance signals at 680, 720, 760 and 800 nm. Oxygen saturation is determined with a calibration curve defined for the derivative value. |
| Location of Measurement | Two-dimensional area of superficial microvasculature | Single point of superficial microvasculature |
| Measurement Sensor | Noninvasive, non-patient-contacting instrument head illuminates the surface and receives returned light. | Noninvasive, patient-contacting probe |
| Output Display | Numeric<br>Two-dimensional color-coded map of estimated oxygenation | Numeric |

Prompts the operator to repeat the measurement if any parameter is found to be outside operating tolerance The hyperspectral scanning method used by the OxyVu-1 provides two-dimensional mapping of color-coded oxygenation levels. The Inspectra uses wavelengths shifted further towards the near-infrared so should sample deeper tissues. The differences in hemoglobin calculations are minor because both devices report an approximate value for subsurface oxygen saturation.

The following examples illustrate embodiments of the invention, but should not be viewed as limiting the scope of the invention.

EXAMPLES OF THE INVENTION

Comparison Study Protocol

Studies were performed with human subjects to demonstrate performance equivalent to that of the predicate device.

The primary study demonstrated performance of the OxyVu-1 system in normal and ischemic conditions. Test results were then compared to published data for a similar study that used the predicate device. Repeated, steady-state, measurements taken during the primary study were analyzed to demonstrate precision. During the primary study, $TcPO_2$ (transcutaneous oxygen pressure) measurements were made adjacent to the areas scanned with the OxyVu-1 system. The instrument used was a Perimed PF 5040 $TcPO_2/CO_2$ system. The $TcPO_2$ data provide an indication of the tissue conditions, but cannot be rigorously compared to the OxyVu-1 data.

The Perimed sensors were immediately adjacent to, but not in the area scanned by the OxyVu-1 system. The Perimed sensors measures partial pressure of oxygen in the subcutaneous tissue bed; the OxyVu-1 measures hemoglobin in the capillaries. The Perimed sensors heat the skin surface; the OxyVu-1 does not heat.

A short, secondary study was performed to demonstrate the comparability of OxyVu-1 measurements to the Perimed $TcPO_2$ measurements. Immediately after a Perimed measurement was made, the OxyVu-1 scanned the area of the Perimed measurement.

Primary Study Protocol

The goal of this clinical study was to show the performance of the OxyVu-1 system in measuring tissue hemoglobin oxygen saturation. HT-Sat values were measured in superficial tissue of the forearm and foot during timed stages of alteration of the circulation achieved by application of moderate and high constriction pressures. Constriction pressures were induced by applying pressure proximal to the measurement site. Pressure was applied safely using a wide blood pressure cuff.

The procedure began with 10 minutes measuring at baseline (p=0), then 10 minutes with the cuff inflated, followed by 15 minutes with the pressure release. The pressure cuff was deflated immediately if a subject expressed significant discomfort. One study was terminated early because of such discomfort.

Measurements were performed on the forearm and the dorsum of the foot around the first metatarsophalangeal joint in twelve subjects. Subjects were enrolled from a wide cross-section of the population, e.g., 18 to 85 years of age, males and females, varying skin types, varying racial origins, and with and without chronic diseases such as diabetes.

Three Perimed $TcPO_2$ electrodes recorded oxygen tension (mmHg) continuously. One was placed proximal to the field of view of the hyperspectral scanner, one distal, and one midway but outside the field of view. The electrodes were held in place using adhesive fixation rings, which were then filled with a contact solution to couple to the electrode.

The OxyVu-1 system collected hyperspectral scans every minute during the procedure. The scans were later processed to produce maps. The system calculated mean values of tissue oxygenation parameters from a small region at the center of the scanned area. A small adhesive label (target) was placed on skin in the field and was used as a fiduciary for registering the scan. Both instruments had time stamps for direct time comparisons.

Secondary Study Protocol

To demonstrate the relationship between HT-Sat measurements (which reflects oxygen binding to hemoglobin) and $TcPO_2$ measurements (which reflects free tissue oxygen), a Perimed $TcPO_2$ measurement was made and then immediately scanned the area with the OxyVu-1. Two sets of forearm measurements with each of six subjects.

The Perimed $TcPO_2$ probe heats the site to 44° C. to make its measurement. The OxyVu-1 scans were made immediately after removal of the Perimed probe. The mean HT-Sat values were taken within the red central spot and were compared to the $TcPO_2$ values measured at that spot.

Summary of Results

The OxyVu-1 was consistently sensitive to ischemic conditions, tracking with the $TcPO_2$ measurements with the exception of an HT-Sat overshoot at release of the cuff pressure not seen in the $TcPO_2$ measurements. This rebound is caused by a transient dilation response as blood flow returns to the capillaries. The Perimed $TcPO_2$ sensor heats the tissue, dilating the capillaries. With capillaries already dilated, there can be no additional reperfusion dilation.

Figure 5:
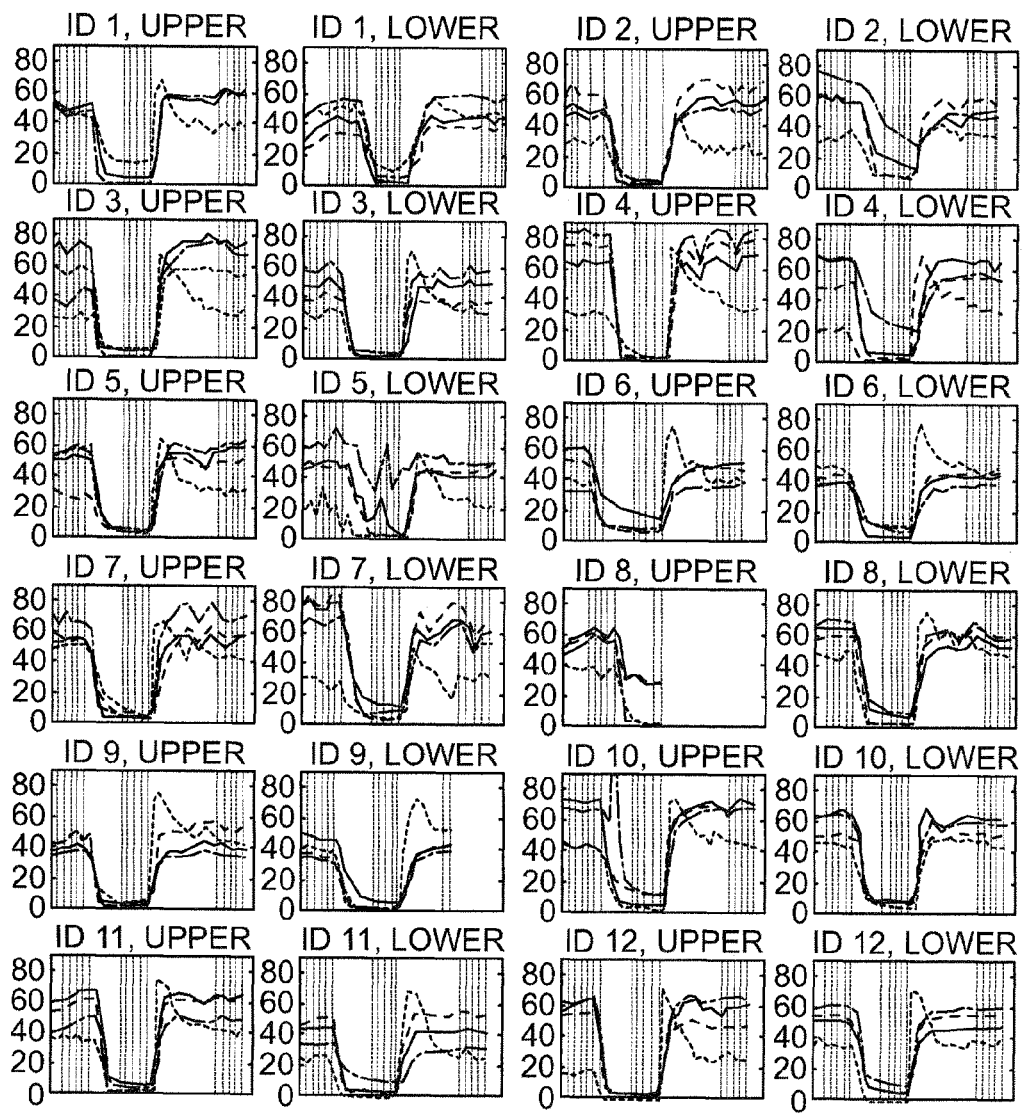
FIG. 5 Charts from the 12 study subjects showing HT-Sat measurements collected every minute and continuous $TcPO_2$ readings.

Charts from the 12 study subjects showing HT-Sat measurements collected every minute and continuous $TcPO_2$ readings (see FIG. 5). The x axis represents time in minutes and the y axis represents percent oxygen saturation for HT-Sat measurements and mmHg for $TcPO_2$ measurements. Above each chart is recorded the patient identification number and the extremity measured. HT-Sat measurements (volar forearm for upper extremity and foot dorsum for lower extremity) are represented in black. $TcPO_2$ measurements are represented in blue, red, and green (upper extremity: proximal volar forearm (blue), distal volar forearm (green) mid dorsal forearm (red) and lower extremity: lateral foot dorsum (green), lateral calf (blue), medial malleolus (red). Simultaneous measurements utilized in the static analysis are represented by the dotted lines.

The OxyVu-1 system's sensitivity to ischemia was demonstrated by comparing the stable state means (the means of the last five measurements in each phase). Stable state means were compared to remove transient effects which would be seen in this artificially induced ischemia of this study, but not in a normal patient examination. The difference is significant ($p<0.0001$).

Upper and lower extremity measurements of percent hemoglobin saturation (HT-Sat), and the relative oxyhemoglobin (HT-Oxy) and deoxyhemoglobin (HT-Deoxy) levels collected with the OxyVu-1 during pressure cuff ischemia experiment. Results are compiled in Table 4.

TABLE 4

Upper and lower extremity measurements of percent hemoglobin saturation (HT-Sat), and the relative oxyhemoglobin (HT-Oxy) and deoxyhemoglobin (HT-Deoxy) levels collected with the OxyVu-1 during pressure cuff ischemia experiment

| | | All Subjects (n = 12) (mean ± SD) | | |
|---|---|---|---|---|
| Site | State | HT-Sat (%) | HT-Oxy | HT-Deoxy |
| Upper Extremity/ Forearm | Baseline | 35 ± 10 | 47 ± 14 | 88 ± 27 |
| | Ischemia | 5 ± 5 | 6 ± 6 | 143 ± 44 |

TABLE 4-continued

Upper and lower extremity measurements of percent hemoglobin saturation (HT-Sat), and the relative oxyhemoglobin (HT-Oxy) and deoxyhemoglobin (HT-Deoxy) levels collected with the OxyVu-1 during pressure cuff ischemia experiment

| | | All Subjects (n = 12) (mean ± SD) | | |
|---|---|---|---|---|
| Site | State | HT-Sat (%) | HT-Oxy | HT-Deoxy |
| | Recovery | 36 ± 7 | 47 ± 15 | 83 ± 22 |
| Lower Extremity/ | Baseline | 35 ± 11 | 40 ± 15 | 72 ± 15 |
| Foot Dorsum | Ischemia | 4 ± 5 | 6 ± 7 | 130 ± 45 |
| | Recovery | 37 ± 9 | 44 ± 14 | 73 ± 16 |

In a published study of the predicate device, InSpectra Model 325, using a similar induced ischemia protocol, the predicate device showed similar sensitivity to ischemia. As shown in table 5, Inspectra 325 hemoglobin percent oxygen saturation measured in the extremity of normal subjects during pressure cuff induced acute ischemia.

TABLE 5

Inspectra 325 hemoglobin percent oxygen saturation measured in the extremity of normal subjects during pressure cuff induced acute ischemia.

| Site | State | % StO2 (mean ± SD) (n = 26) |
|---|---|---|
| Upper Extremity/ | Baseline | 82 ± 10 |
| Dorsal Forearm | Ischemia | 6 ± 11 |
| | Recovery | 80 ± 10 |
| Lower Extremity/ | Baseline | 86 ± 7 |
| Tibialis Anterior | Ischemia | 19 ± 17 |
| | Recovery | 85 ± 7 |

Indicated saturation levels are essentially the same for ischemia as measured by both the OxyVu-1 and the Inspectra 325. There is a systematic difference between the two devices in baseline and recovery measurements. Differences in saturation values are related to known perfusion differences between the tissues measured by the two devices.

Both instruments are substantially equivalent in their ability to distinguish ischemia as shown in Table 6.

TABLE 6

Comparison of OxyVu-1 and Inspectra 325 (data derived from separate cuff ischemia experiments).

| | | Tissue hemoglobin oxygen saturation (mean ± SD) | |
|---|---|---|---|
| Site | State | OxyVu-1 (n = 12) | Inspectra 325 (n = 26) |
| Upper | Baseline | 35 ± 10 | 82 ± 10 |
| Extremity | Ischemia | 5 ± 5 | 6 ± 11 |
| | Recovery | 36 ± 7 | 80 ± 10 |
| Lower | Baseline | 35 ± 11 | 86 ± 7 |
| Extremity | Ischemia | 4 ± 5 | 19 ± 17 |
| | Recovery | 37 ± 9 | 85 ± 7 |

OxyVu-1 precision was measured by considering the repeated "static" measurements (the last five measurements) in both baseline and recovery. Standard deviations were calculated for each patient and site. The median standard deviation is about 2, much less than what would be a clinically significant difference in oxygen saturation.

The median of the estimates of standard deviation for HT-Sat for two sites and two states in shown in Table 7.

TABLE 7

| Site | State | Median Standard Deviation | Median STD |
|---|---|---|---|
| Upper Extremity | Baseline | 1.78 | 1.95 |
| (Volar Forearm) | Recovery | 2.06 | |
| Lower Extremity | Baseline | 1.85 | |
| (Foot Dorsum) | Recovery | 1.97 | |

Figure 6:
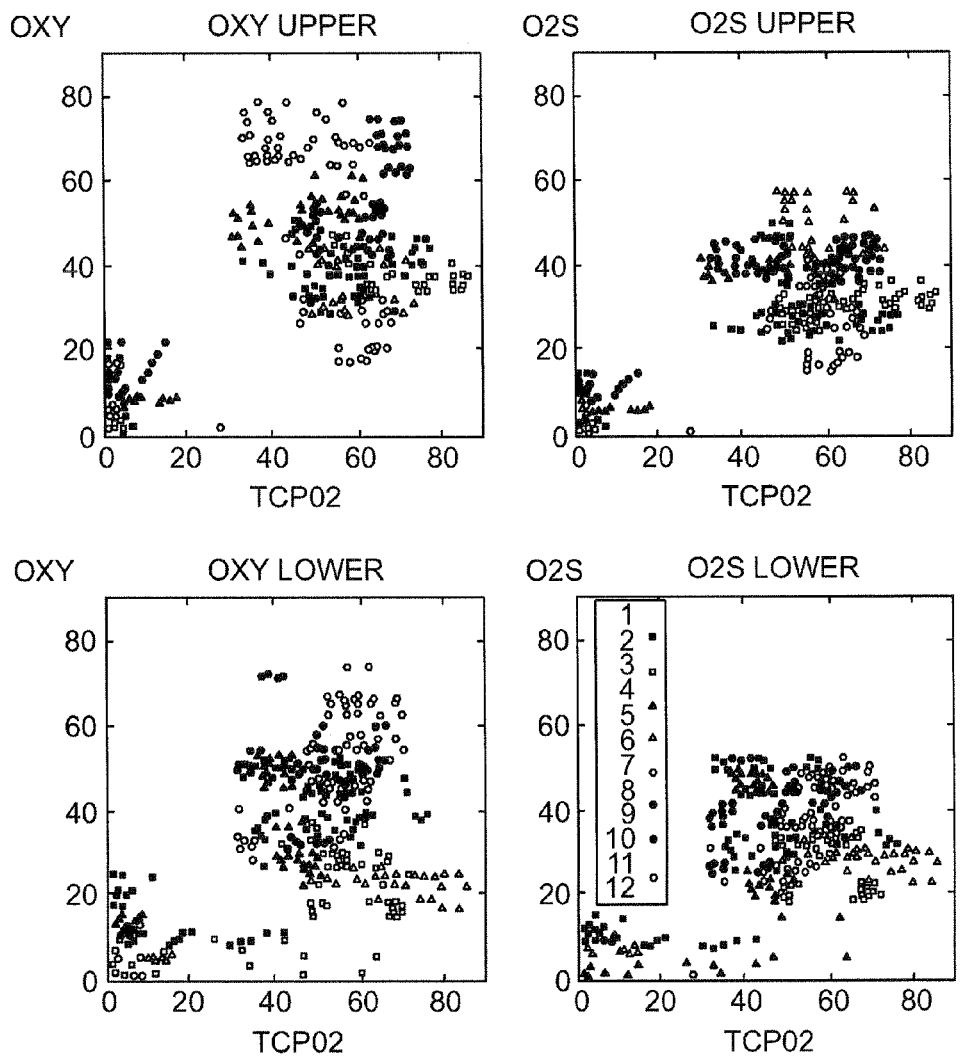
FIG. 6 Scatter plots demonstrate correlation between HT-Sat and $TcPO_2$ measurements.

Comparison of OxyVu-1 measurements and TcPO2 measurements taken during the stable state times of the primary study shows a correlation as seen in the scatter plots of FIG. 6. The comparison is difficult because the measurements are taken at different locations and because the physiological relationship between hemoglobin oxygen saturation and the oxygen tension is not linear. Note: for each subject's data there is generally larger scatter of $TcPO_2$ measurements. The relationship is shown in the oxyhemoglobin dissociation curve depicted in FIG. 7 as comparison of the OxyVu-1 HT-Sat measurements to the $TcPO_2$ values. The solid lines represent hemoglobin binding curves at 80 mmHg $pCO_2$ (red) and 60 mmHg pCO2 (blue) demonstrating good agreement. OxyVu HT-Sat measurements were collected immediately after $TcPO_2$ probe removal in 6 subjects on the upper extremity.

Direct comparison is difficult because the measurements are taken at slightly different locations and under different tissue conditions. The physiological relationship between hemoglobin oxygen saturation and oxygen tension requires use of measurements under similar tissue conditions and the use of the relationship described by the oxyhemoglobin dissociation curve. When measurements are taken with the OxyVu-1 system under similar conditions as occur during measurements taken with the Perimed $TcPO_2$ monitor, a relationship can be established relating the OxyVu-1 HT-Sat reading and the partial pressure of oxygen measured by the $TcPO_2$ monitor.

In the secondary study, OxyVu-1 measurements were made immediately following the $TcPO_2$ measurements at the same location and under the same conditions as the $TcPO_2$ measurements and. HT-Sat measurements show general agreement with the $TcPO_2$ measurements.

In conclusion, the studies indicate equivalent sensitivity to ischemia between the OxyVu-1 system and the predicate device, the Inspectra 325. The good agreement between HT-Sat and $TcPO_2$ measurements made under the same conditions, suggest strongly that the OxyVu-1 saturation measurement is sufficiently accurate for clinical purposes.

Software Description

Software controls the functions or the OxyVu-1 system including:
User interface
System control
Calibration
Data acquisition
Measurement and Mapping Algorithm
Storage
Summary of Software Lifecycle/Software Development Plan The Software Development Plan describes the overall methodology for software development. Software is developed in an iterative process providing continual improvement from research prototypes through production prototypes to released product. Superimposed on the iterative process is a "waterfall" tied to the Design Control design reviews.

This description is intended to demonstrate how the software development process works. They reflect documents as approved at the Design Input Design Review, but is expected to evolve through the design cycle.

To demonstrate traceability and verification/validation of software the documents trace requirements for calibration that are implemented in software from requirements to their validation in the clinical trial described in this submittal and to the unit test verification of a calibration function.

OxyVu-1 Cuff-Ischemia Study

To evaluate the responsiveness of the OxyVu-1 to low/no flow ischemia, a cuff-ischemia experiment was performed in normal human subjects on upper and lower extremities. Hyperspectral Tissue (HT) oxygenation measurements of hemoglobin percent oxygen saturation were recorded from dermal sites on the mid volar forearm and central foot dorsum. Twelve subjects were recruited between the ages of 21 and 85 years of age (mean 60 years). There were eight men and four women, eight Caucasians, two African Americans and two Asians. Five patients had diabetes (one Type 1 and four Type 2). The average systolic blood pressure was 126 mmHg (range 110 to 150) and the average diastolic blood pressure was 77 mmHg (range 55 to 90). The average weight was for the men 176 pounds (range 110 to 225) and for the women 167 pounds (range 120 to 235).

Hyperspectral tissue percent hemoglobin oxygen saturation (HT-Sat) was measured with the OxyVu-1. Acute ischemia was induced by inflation of a blood pressure cuff placed proximally on the extremity being measured. Inflation pressures were set to 50 mmHg above the systolic blood pressure, not exceeding 10 minutes. To better assess the performance of the OxyVu-1 on the patient population on which this device is used, elderly patients, diabetics and subjects with elevated systolic blood pressure were not excluded.

One subject had significant discomfort associated with cuff inflation on the lower extremity and that portion of the study was terminated early. One patient's first visit was excluded from the primary analysis for skin temperatures less than 30° C. For temperatures below 30° C., the user manual requires repeat examination at least 4 hours after any caffeine, nicotine or adrenergic agent and with attention to room temperature between 22° C. and 27° C. The excluded patient returned and was studied in accordance with user manual recommendation and the second visit was included in the analysis.

An Inspectra 325, the predicate device was not available. To compare with another known measurement technique, $TcPO_2$ measurements were collected with a Perimed PF5040 transcutaneous oxygen monitor. $TcPO_2$ measurements were obtained of three sites on each extremity: proximal volar forearm just below the elbow, distal volar forearm (wrist), mid dorsal forearm, lateral midcalf, medial maleolus, and lateral foot dorsum. Both HT measurements (obtained every minute) and $TcPO_2$ measurements (obtained continuously) were recorded at baseline (10 minutes), during ischemia (10 minutes) and during recovery (15 minutes).

For most subjects, measurements used for the stable-state analysis were taken from the last five minutes of each segment. Similar to data previously presented on the performance of the Inspectra 325, the primary analyses that follow pertain to a specified subset of the data wherein dynamic changes due to the introduction and release of ischemia were minimal. These data are referred to as the stable-state data. The dotted vertical lines in FIG. 5 indicate the values included in the stable-state analysis. The several exceptions to this were related to subject motion (subject 2) and incomplete studies due to subject discomfort (subject 8) and instrument dysfunction requiring recalibration (subject 9).

While the stable-state data provide a clearer comparison of our data with the Inspectra 325 data, also analyzed were the complete set of data including the time interval in which ischemia begins and ends. The analogous summaries for the complete data do not differ in any substantial way from the summaries for the static-state data except that as expected, the dynamic change due to ischemia make the standard deviations larger. Some properties of the full dataset shows the goodness of fit as measured by explained variation (R-squared) comparing HT-Sat with $TcPO2$ measurements. These data support the assertion that measurements closely correlate with an established method for measuring changes in tissue oxygenation induced by ischemia.

For the stable-state data, HT-Sat baseline measurements averaged 35% ($\pm$10 SD) in the upper extremity and 35% ($\pm$11 SD) in the lower extremity and were not dependent on location. With ischemia, HT-Sat dropped to an average value of 5% ($\pm$5SD) in the upper extremity and 4% ($\pm$5SD) in the lower extremity. Recovery HT-Sat values were identical to baseline values averaging 36% (+7SD) in the upper extremity and 37% ($\pm$9SD) in the lower extremity. These data are summarized in Table 4. Mean and standard deviations for HT-Sat, HT-Oxy, and HT-Deoxy measures at baseline, ischemia, and baseline following ischemia are given in Table 4.

The charts for all 12 studies are provided in FIG. 5. To find the stable-state means and standard deviations for the three measurement conditions (baseline, ischemia, and recovery), the vertical dotted lines in FIG. 5 represent the times where data points were used in the analysis presented in Table 4. In other words, the dynamic times where the values shift towards ischemia, rebound following release of ischemia, and shift back to baseline are not included in the primary analysis.

The HT measurements clearly demonstrated a stable baseline, a consistent decrease with low/no flow, an overshoot associated with reperfusion followed by a return to a level after ischemia similar to baseline. Steady state measurements appeared stable at the end of each step can measure ischemia and/or perfusion. OxyVu-1 showed consistently lower tissue hemoglobin oxygen saturation during ischemia compared to baseline and recovery states. The analysis is described below with the difference found to be statistically significant ($p<0.0001$).

OxyVu-1 Precision

In statistical science, precision is defined as the reciprocal of the standard deviation. Ideally, precision measures the variation expected in a device measurement at a specific moment in time. This ideal was approximated by taking a short series of adjacent measurements during states when HT-Sat was relatively undisturbed, that is, during baseline and late during recovery. Precision was assessed by taking the standard deviation of consecutive measurements taken at one minute intervals when HT-Sat was at its baseline level and similarly, near the end of the recovery period. For this assessment, excluded from the static-state data were the measurements obtained during the ischemic period because HT-Sat had been dynamically disturbed. In particular, for subject at each site only the last five measurements in the baseline and recovery states were used. Forty seven estimates were obtained of the standard deviation with 12 subjects, 2 sites, and 2 states. One subject at one site was not measured during recovery. The baseline median standard deviations for arm and leg were 1.78 and 1.85, while the recovery median standard deviations for arm and leg were 2.06 and 1.97. Combining all sites and states, the median standard deviation was 1.95.

TABLE 8

The median of the estimates of standard deviation
for HT-Sat for two sites and two states

| Site | State | Median Standard Deviation | Median STD |
|---|---|---|---|
| Upper Extremity (Volar Forearm) | Baseline | 1.78 | 1.95 |
| | Recovery | 2.06 | |
| Lower Extremity (Foot Dorsum) | Baseline | 1.85 | 1.97 |
| | Recovery | 1.97 | |

Comparison to Predicate Device—Inspectra 325

As stated, HyperMed performed the above test of the OxyVu-1 to demonstrate substantial equivalence to the Inspectra 325, Hutchinson Technologies, Inc. Given the inability to procure chosen predicate device for simultaneous data collection, describe here are historical results of a cuff ischemia experiment performed with the Inspectra 325 under similar experimental conditions. A comparison of the Inspectra 325 data is provided to the OxyVu-1 data reported above.
Reported Inspectra 325 Study In a fashion similar to the experiment above, an experiment was performed with the OxyVu-1 System, Hutchinson Technology's previously reported a tourniquet-induced ischemia experiment in normal human subjects to establish responsiveness to low or no flow ischemia. Hemoglobin percent oxygen saturation measurements were recorded in superficial muscles in the arm and legs. Twenty-six subjects were enrolled between the age of 27 and 56 years. Percent hemoglobin oxygen saturation was measured with an Inspectra Model 325 tissue spectrometer (Hutchinson Technology). Depending on location, probes having different source-detector separation distances were used. The tissue sites measured were the thenar eminence, dorsal forearm and tibialis anterior using 12, 20 and 25 mm probe separation distances, respectively. The probe was held in contact with skin using an adhesive pad that shields the probe from extraneous room lights. Acute ischemia was induced by inflation of a blood pressure cuff placed proximally on the extremity being measured. Inflation pressures were set to 55 mmHg above the systolic blood pressure, not exceeding 15 minutes. In the Inspectra 325 study, the investigators chose to exclude subjects with systolic pressures above 140 mmHg.

Oxygen saturation was measured at baseline, ischemia and recovery. Ischemia was based on measurements at least 5 minutes after inflation. Baseline measurements averaging 82%±10SD in the upper extremity and 86%±7SD in the lower extremity and were not dependent on location. With ischemia, oxygen saturation dropped to an average value of 6%±10SD in the upper extremity and 19%±17SD in the lower extremity. Recovery values were identical to baseline values averaging 80%+10SD in the upper extremity and 85% f 7SD in the lower extremity. These data are summarized in Table 5.

The study concluded that the Inspectra 325 showed consistently lower tissue hemoglobin oxygen saturation during ischemia compared to baseline and recovery states. The difference was found to be statistically significant (p<0.01).
Comparison of OxyVu-1 to Inspectra 325

Based on the results of the similar OxyVu-1 and Inspectra 325 cuff-ischemia experiments, Table 1 was constructed. Note that while the absolute values for the tissue saturations are different due to the differences in tissues examined by the two techniques, in both cases the instruments demonstrated a decrease in tissue saturation with low/no flow ischemia with cuff compression and a subsequent return to baseline with cuff release.

Table 6 shows results for three states and two sites. The equality of means was tested using a two factor ANOVA, with factors state and site. Means were compared using Tukey's test for pair-wise comparisons. The comparison between sites and between baseline and recovery states did not differ significantly. The ischemia state differed significantly from both baseline and recovery states with p<0.0001.

As expected from previous published results, the subsurface tissue measured by OxyVu-1 demonstrates dermal saturations in the 25 to 50% range. In keeping with reported data, a higher hemoglobin oxygen saturation is expected from muscle tissue. In this comparison, while the dermal HT-Sat measurements are consistently lower than the Inspectra measurements collected from the deeper muscular tissue, both instruments similarly show a statistically significant decrease in tissue hemoglobin oxygen saturation associated with ischemia. It was concluded that, like the Inspectra predicate, OxyVu-1 showed consistently lower hemoglobin percent oxygen saturation during ischemia compared to baseline and baseline following recovery states and that this difference was found to be statistically significant (p<0.0001).
Comparison of OxyVu-1 to $T_cPO_2$ In the absence of the availability of the Inspectra 325 device, to provide simultaneous comparison with another known measurement technique, $TcPO_2$ measurements were collected with a PF5040 Transcutaneous Oxygen Monitoring System (Perimed, Inc.) throughout the pressure cuff-ischemia study. After the prescribed warm-up period, continuous measurements were recorded at three sites on the upper extremity (proximal volar forearm, distal volar forearm, mid dorsal forearm) and three sites on the lower extremity (lateral foot dorsum, lateral calf, and medial maleolus). FIG. 6 presents scatter plots comparing OxyVu-1 measurements to $TcPO_2$ measurements for the time points indicated by the vertical dotted lines in FIG. 5.

Note that there is significant scatter in the $TcPO_2$ measurements for each individual and that many outlier points in the lower two panels of FIG. 6 (oxy and o2s<10 when $TcPO_2$>20) relate to the lateral dorsum position of the $TcPO_2$ monitor especially for subjects 2, 4 and 5 (see red line for these subjects in FIG. 5). In this location we frequently could not get a reliably flat surface as is recommended by the manufacturer and given the readings from the two other sites we can consider that the lateral foot $TcPO_2$ readings to be falsely high.

The scatter plots show an overall tendency for HT-Oxy (oxy) and HT-Sat (o2s) to track with the $TcPO_2$. The analysis in the section that follows further clarifies these associations by incorporating the time of the observation.
Additional statistical analysis comparing HSI to $TcPO_2$ Data For this analysis, the entire dataset was first divided into two subsets, a subset for the dynamic period between 8 minutes and 22 minutes during which all subjects began and ended ischemia and a subset of the remaining times before and after this dynamic period. Here are reported only on the analysis of the data for the dynamic period. The $TcPO_2$ measurements are compared with HT-Sat measurements to assess goodness of fit as evidence that $TcPO_2$ tracks with HT-Sat The goodness of fit criterion was R-squared, the proportion of total variation explained by the ANCOVA (ANOVA with added covariates) model. In this context R-squared is a direct generalization of simple Pearson correlation.

An overall goodness of fit analyses was done and also 12 separate analyses were done, one analysis per subject.
Analysis of the Dynamic Ischemic Period The dynamic periods starts at the onset of ischemia, includes the rebound following reperfusion, and ends with the recovery to baseline. The interval from 8 minutes to 22 minutes into the study usually contained the ischemic state. Typically, the pressure cuff was inflated at 10 minutes and deflated at 20 minutes. In analyzing the dynamic period, there were three issues:

Dependency Among Repeated Measures Over Time $TcPO_2$ was measured at three separate anatomic subsites on the upper extremity and three separate subsites on the lower extremity. The HT-Sat appeared to rebound after ischemia stopped (the graphs reach a high peak near 21 minutes and then decline towards stability) whereas the $TcPO_2$ did not. (The $TcPO_2$ graphs resemble square waves and have no peaks).

Methods

To deal with time dependency, two ANCOVA models were run, one with and one without covariance structure to account for repeated measures over time. If the covariates in the two models had similar regression coefficients, they were reported as R-squared for the model without covariate structure as the measure of goodness of fit.

To deal with the three measurement sites for $TcPO_2$ for each extremity, each $TcPO_2$ site was analyzed separately and then pooled all $TcPO_2$ sites into one overall analysis. If the covariates in the separate and overall analyses had similar regression coefficients and would be reported R-squared for the overall model.

For the dynamic ischemia period analysis, to deal with the peaks and rebound pattern in the HT-Sat data that appeared between 19 and 22 minutes, two general (not subject-specific) terms were added to the model; namely, a binary factor, t1922, defined as 1 at times from 19-22 minutes and zero elsewhere, and a linear spline factor, $t21=|time-21|$, that reversed direction at time 21 defined only on the interval of times from 19-22.

Adding only two terms to the dynamic model the peak and rebound effects provides a conservative goodness of fit. It could improve the fit by varying the time when HT-Sat peaked to match the subject rather than fix that time as time 21.

The outcome for each of the dynamic and static ANCOVA models was HT-Sat. The predictors were site (upper vs. lower extremity), a class factor for the three subsites on each extremity, t21, t1922, and the linear factor time. For the overall analysis the categorical factor, id, was a random effect. Included were selected interaction terms depending on the model. None were highly significant and thus were excluded in their descriptions. The class variable for $TcPO_2$ subsite is not described hereafter for the same reason.

Results

The analysis was carried out to evaluate the tracking of HT-Sat and $TcPO_2$ during the dynamic period and to assess whether both have flat profiles during the stable periods. The overall $TcPO_2$-pooled analysis has the same qualitative results as the 12 separate subject specific analyses.

Overall Equivalence of Models with and without Repeated Measures

Table 9 shows the results for the repeated-measures ANCOVA model and the simple ANCOVA model. The regression parameters are very similar indicating the insensitivity of the estimated regression coefficient to the repeated measures structure. The variable $TcPO_2$ was highly significant in the two models, as were the variables, t1922 and t21, the adjustments for the peak and rebound. The linear factor, time, was either not significant or slightly significant.

TABLE 9

Dynamic Period Regression Coefficients for the Repeated Measures and Simple ANCOVA models.

| | Repeated Measures Model | | | Simple |
|---|---|---|---|---|
| Variable | Estimate | StdErr | Pvalue | Estimate |
| $TcPO_2$ | 0.538 | 0.0208 | <.0001 | 0.496 |
| t1922 | 43.830 | 2.0302 | <.0001 | 46.719 |
| t21 | −19.130 | 1.0177 | <.0001 | −19.915 |
| Time | −0.238 | 0.1616 | 0.1412 | −0.476 |
| Site | −2.972 | 1.6320 | 0.0729 | −2.777 |

For the dynamic-period, the $TcPO_2$ estimate of the regression coefficient was 0.538 in the repeated-measures model and 0.496 in the simple ANCOVA model. The other estimates also closely matched. The variables 'time' and 'site' were not significant. The differences among the means of the three anatomic $TcPO_2$ subsites were not significant.

For the dynamic period, because the repeated measures structure had little effect on these coefficients, we used the value of R-squared=0.76 for the simple ANCOVA model to assess overall goodness of fit. This value strongly supports the equivalence of HT-Sat and $TcPO_2$ measurements. This value is conservative. The simple ANOVA was run on each at each of the two sites for each of the 12 subjects to obtain a subject-site specific model. Over these 24 models the values of R-squared averaged 0.87 and ranged from 0.43 to 0.97. It was concluded that HT-Sat tracks with $TcPO_2$ during the dynamic period.

Additional Considerations

Motion

Figure 8B:
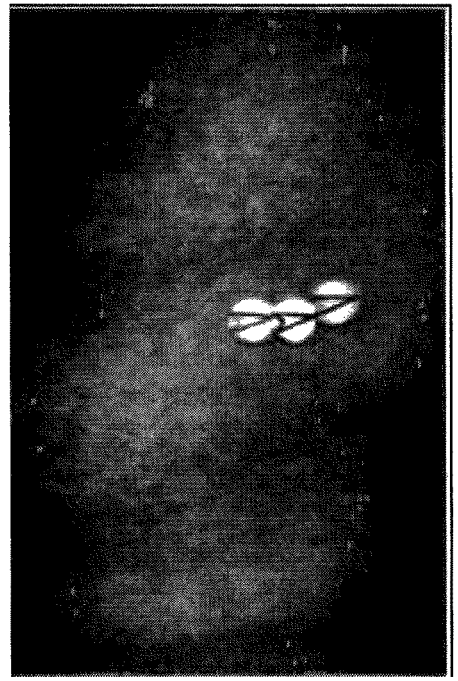
FIG. 8 Example of reflectance image recorded from a stationary site (panel a) and during involuntary motion of the same site (panel b) that occurred in three jerks during 200 milliseconds one minute later during the cuff-ischemia study (Subject 2). The image displayed in panel b) was excluded from analysis.
Figure 8A:
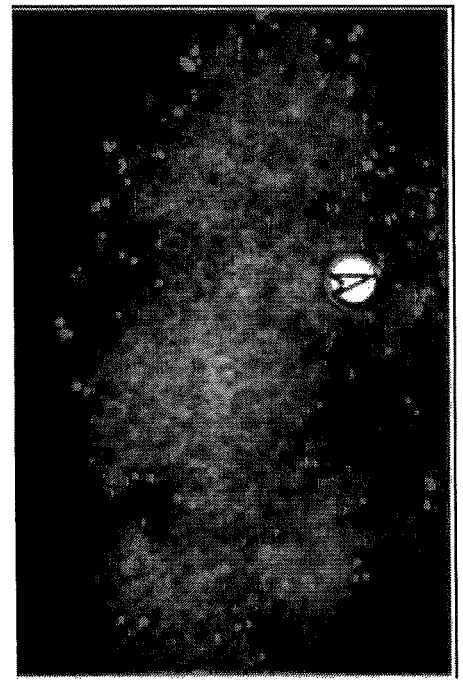

In the pressure-cuff ischemia study, prior to analysis, approximately 0.5% of measurements were excluded from further consideration due to substantial motion artifact visible on the images recorded, as is recommended in the user manual. If a subject does not move during a single image acquisition (~100-200 millisecond), the acquired image displayed on the computer screen looks like the image in FIG. 8(a) and is considered adequate. Sometimes if the body part under examination is not well supported or due to an underlying patient neuromuscular condition, an involuntary motion occurs within part of a second. In that case, the camera will record a smeared image of skin, such as in FIG. 8(b), where the same subject has moved in three jerks during the image period. Such an image would not be considered to provide suitable information.

In standard operation of the device, the technician is instructed in the operator manual to exclude any image with more than one OxyVu Target or an OxyVu Target that appears smeared or out of focus.

Several $TcPO_2$ measurements per subject were also excluded when abrupt changes were noted associated with patient motion displacing the probe or leading to other probe related issues such as outside air leaking into the space between probe and skin. In standard operation, these measurements would be excluded as well.

Relationship Between HT-Sat and $TcPO_2$ Measurements

When measurements are taken with the OxyVu-1 system under similar conditions as occur during measurements taken with the Perimed $TcPO_2$ monitor, a relationship can be established relating the OxyVu-1 HT-Sat and the partial pressure of oxygen measured by the $TcPO_2$ monitor. OxyVu-1 HT-Sat measurements, normally taken at room temperature (22-27° C.), reflect the normal state of the tissue. The Perimed $TcPO_2$ measurements, taken at 44° C. to induce vasodilatation and oxygen release from the tissues, reflect an abnormal state.

Figure 9A:
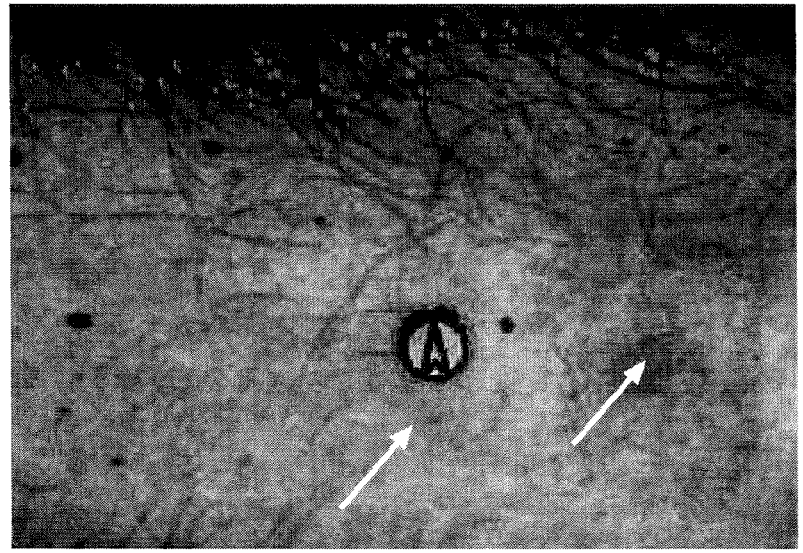
FIG. 9 Hyperspectral analysis of temperature-induced hyperemia induced by the $TcPO_2$ probe. Absorption spectral for the hyperemic site (right arrow in panel a) and an uninvolved area (left arrow in panel a).
Figure 9B:
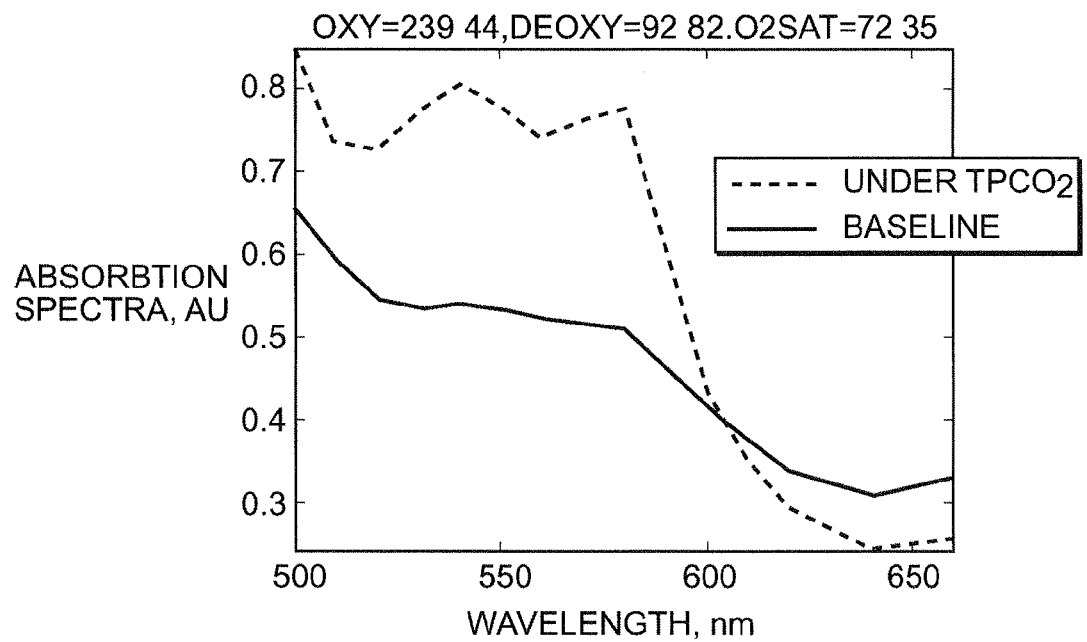

To demonstrate the relationship between OxyVu-1 HT-Sat and Perimed $TcPO_2$ measurements, HT-Sat data was collected immediately after the $TcPO_2$ probe was lifted off the skin. A visual image and OxyVu spectra are demonstrated in FIG. 9(a). The red spot to the left of the OxyVu Target is the mark created by heating by the $TcPO_2$ probe. Two points are taken for comparison: one from the middle of the $TcPO_2$ mark (right arrow) and the second from the undisturbed skin (left arrow). The absorption spectra recorded from the two points are shown in panel b). The skin under the $TcPO_2$ probe shows much higher hemoglobin saturation compared to the baseline skin. For the baseline skin, the HT-Sat was 35%. For the vasodilated area, heated by the $TcPO_2$ probe, the value for HT-Sat was 72%.

Figure 7:
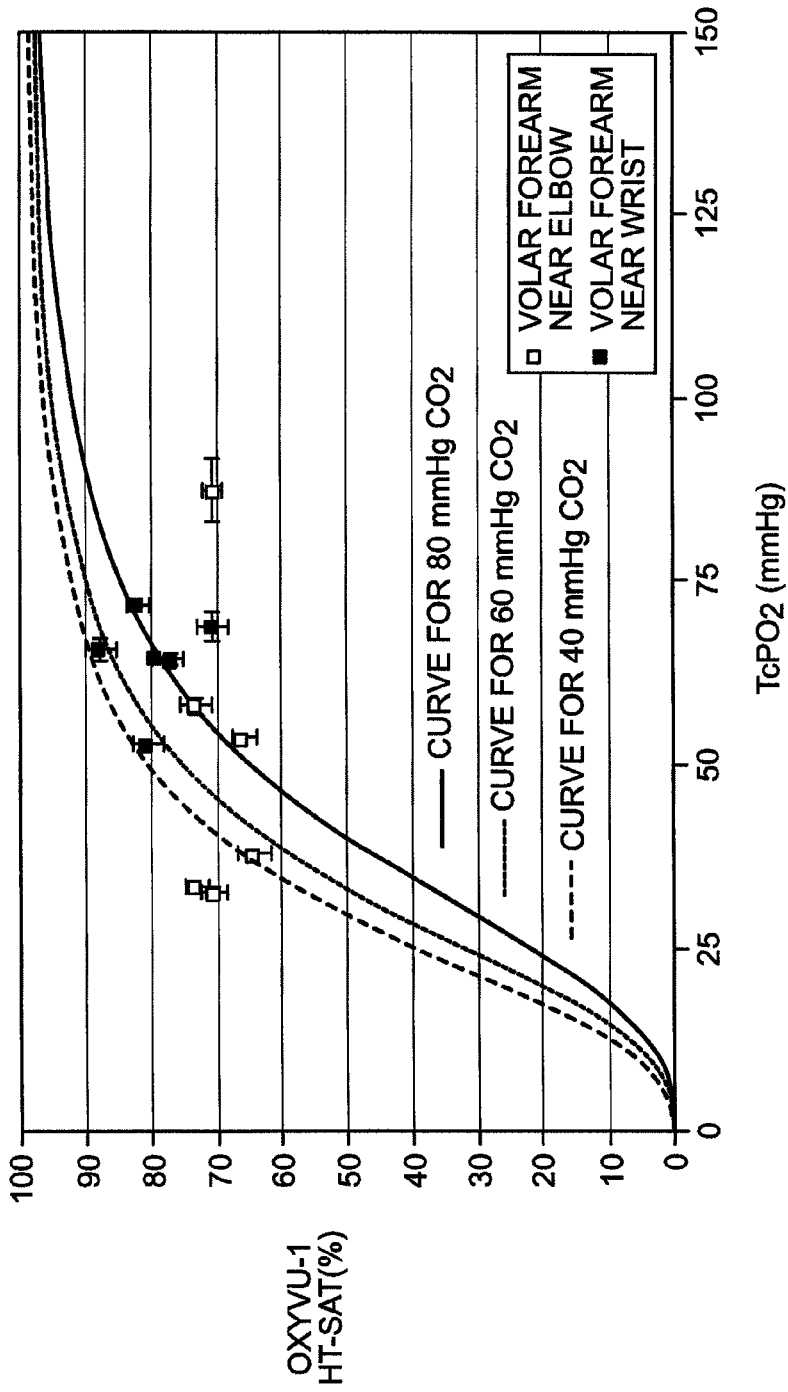
FIG. 7 Comparison of the OxyVu-1 HT-Sat measurements to the $TcPO_2$ values. The solid lines represent hemoglobin binding curves at 80 mmHg $pCO_2$ (red) and 60 mmHg pCO2 (blue) demonstrating good agreement.

In FIG. 7, the mean HT-Sat values were taken within the red central spot just after removing the $TcPO_2$ probe and were compared to the $TcPO_2$ values measured just prior to removing the probe. The green points were measured at the volar wrist and, the magenta at the volar forearm just below the elbow. The black curve is the cooperative binding curve for hemoglobin when the $pCO_2$ is 40 mmHg (normal blood $pCO_2$). The blue curve is the cooperative binding curve for hemoglobin when the $pCO_2$ is 60 mmHg while the red curve is the curve when the $pCO_2$ is 80 mmHg. Overall, the HT-Sat values are in good agreement with the expected value based on the binding curves. The $pO_2$ for the wrist is somewhat high and may suggest the $pCO_2$ is a little higher at the wrist. The outlier at the elbow may represent a probe seal that was not tight.

Reperfusion

Increased flow and increase in tissue saturation associated with reperfusion is a commonly described phenomenon and are demonstrated by the HT-Oxy measurements obtained immediately following cuff release. These changes are not reflected in the $TcPO_2$ monitor, where the skin has been heated and artificially vasodilated throughout the procedure. The reperfusion effect that was seen following cuff-pressure release (from 35% to 70%) is similar in magnitude to what was reported for control subjects (from 35% to 50%) in which acetylcholine ionophoretically was applied, and similar to what is observed with other techniques reporting tissue oxygen saturation.

Temperature

In hundreds of subjects, there was no significant temperature dependence in individuals with skin temperature measurements between 30° C. and 35° C. To avoid complex instructions for clinical use, a screening method was developed to exclude potentially inaccurate measurements. While it is known that certain chemicals and medications such as, for example, caffeine, tobacco and adrenergic drugs such as albuterol are vasoconstrictors, abstinence prior to testing is not routinely required. As a safeguard against potentially inaccurate measurements, and to fall within ranges validated in other large studies, it was recommend that if the skin temperature is outside the normal skin measurement range of 30° C. to 35° C., it be ascertained whether there has been recent intake of any of the above substances and whether the room temperature is in the recommended range of 22° C. and 27° C. If there has been recent intake, or the room temperature is found to be out of range, the study is repeated under recommended conditions with at least 4 hours of abstinence (or more or less as would be known to those skilled in the art) of ingestion of the certain substances. It is known that 8 hours is typically required to alleviate symptoms associated with alcohol, or 24 hours for symptoms associated with certain steroids. Nevertheless, 30 minutes, 1 hour, 2 hours, 6 hours, 8 hours, 16 hours, 36 hours, 48 hours or longer is sometimes necessary or preferred.

Figure 10:
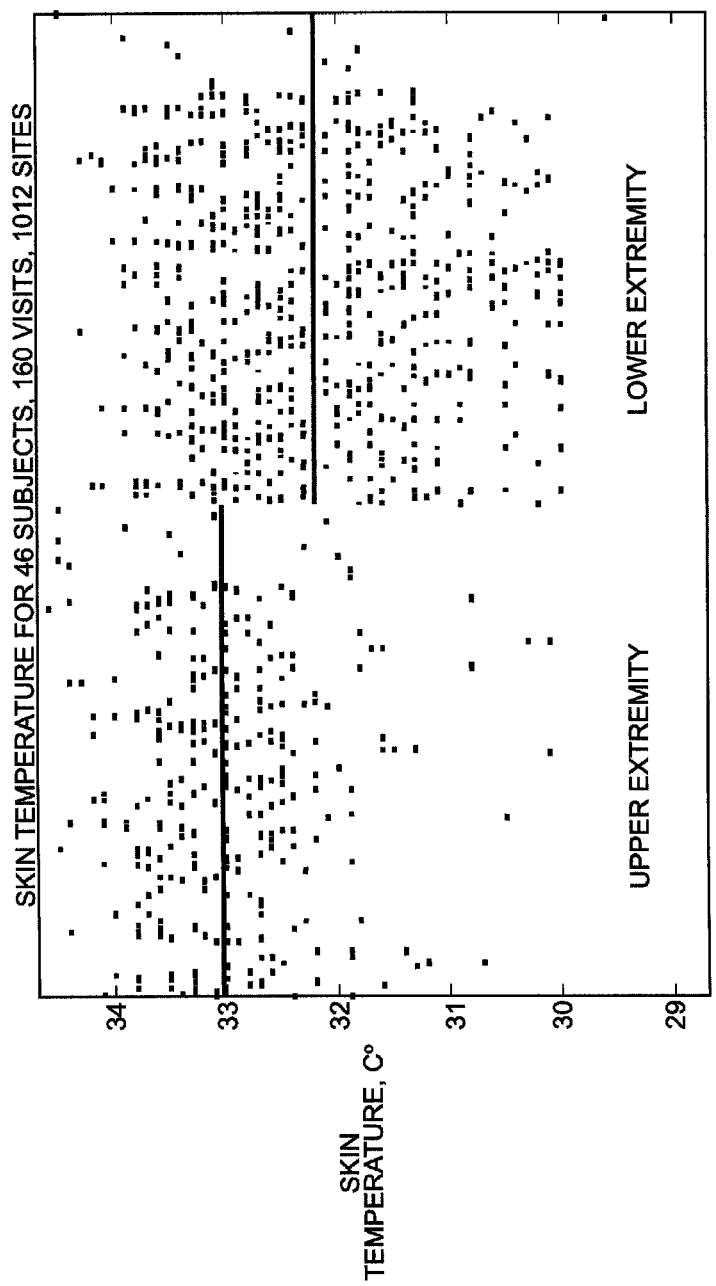
FIG. 10 Skin temperature measurements at 1012 collected from upper and lower extremity sites in 160 study visits of diabetic and non-diabetic.
Figure 12:
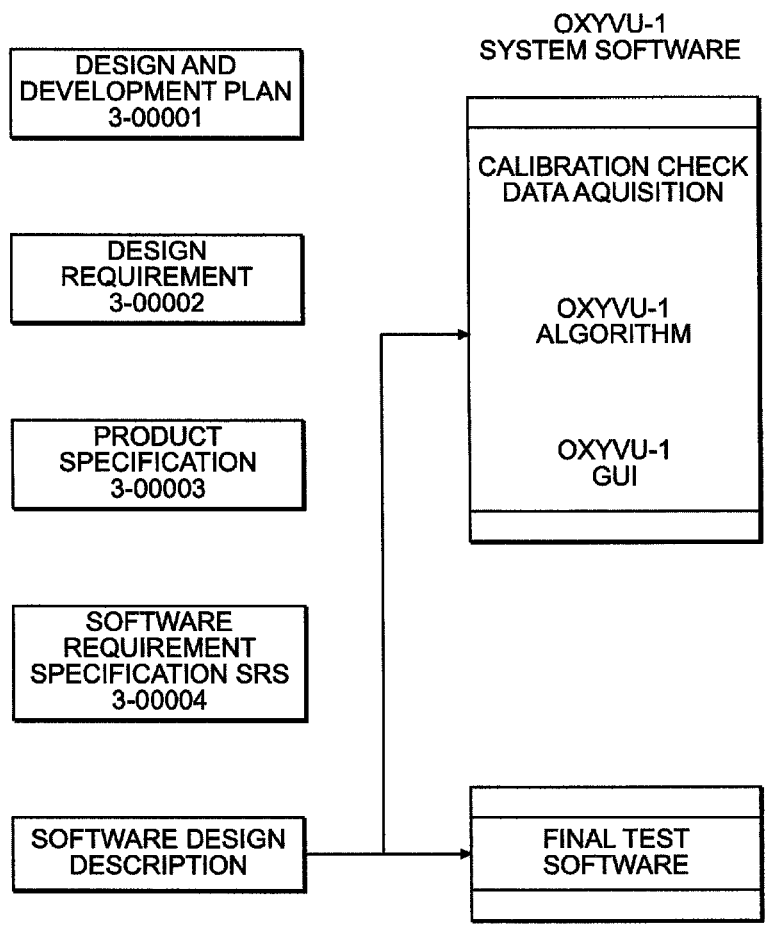
FIG. 12 OxyVu-1 Software Document Structure.

Skin temperature was based on criterion of data from over 160 subject visits recorded as part of an NIH sponsored diabetic foot ulcer study. Room temperature was controlled for as well as caffeine/nicotine/adrenergic substance ingestion. The temperature measurements obtained in that study are presented in FIG. 10.

One subject in the study had foot temperature readings of 28.7° C. for her foot measurements. On that basis, her first study visit was excluded from the analysis. She was asked to return after abstinence from caffeine and nicotine for over four hours. The examination room temperature for the second visit was confirmed to be between 22° C. and 27° C. At the second visit, her foot temperature was 34.4° C. Lower extremity data from first and second visits are presented above.

To confirm that the conclusions achieved were robust for the primary stable-state analyses presented above, the ANOVA was rerun for outcome HT-Sat using the first visit in place the second visit. The results of the analyses were nearly identical. Both analyses showed that state was significant with $p<0.0001$. Both showed that the baseline state did not differ from the recovery state, but the ischemic state differed from both baseline and recovery with $p<0.0001$. The means for HT-Oxy for each state were barely affected. The largest change in the means was a decrease in the baseline and recovery period means of roughly one unit (e.g., from 35 to 34).

OxyVu Software Specifications

The software including user interface to be used on the OxyVu instrument. OxyVu consists of a console and an instrument head. The user positions and focuses the instrument head by overlapping two crossed low power light beams in the center of the field of view. The system acquires hyperspectral data, determines an approximate value for hemoglobin oxygen saturation using a classification algorithm, and presents a map of the tissue hemoglobin oxygen saturation as output for the user. The system also produces a printed report. The system is calibrated with a NIST traceable flat diffuse reflectance standard during manufacture and service. Calibration is validated prior to each patient using a disposable calibration pad.

The software implements the user interface module, data acquisition, process and data analysis algorithms, focusing and illumination evaluation module, pre-patient calibration and calibration checking module, and final test calibration module. The final test calibration software is used in the manufacturing process and during preventive maintenance service. It is used to make pass/fail determinations of the system. All other software modules are used during patient visit to calibrate the system for proper function and to acquire, process and analyze the scan data for tissue characterization.

The OxyVu system provides information as part of a diagnostic protocol in which the information supplements, but does not replace clinical judgment. Preferably, the OxyVu-1 system can be used in conjunction with other diagnostic methods. The OxyVu-1 software indirectly affects the patients because a measurement error would take away one piece of information from the physician's clinical judgment and depending on the significance of the error, make resolution of any inconsistency more challenging. However, because the device is used as a part of a larger, well-understood diagnostic regimen, it can be concluded that the level of concern for the OxyVu-1 software is low to moderate.

System Requirement

The OxyVu software includes a hyperspectral spectral subsystem which enables acquisition of hyperspectral image data for tissue characterization. The hyperspectral scan is acquired using a detector and a wavelength selector (LCTF). The user and the system also make use of the hyperspectral scans for the field of view (FOV) selection or system positioning, system focusing, and system validation using disposable OxyVu Check Pads and OxyVu Targets. The software will support the following hardware functional processes:

General Requirements Include:
- Hyperspectral ScanSubsystem (CMOS detector, LCTF and thermometer).
- Computer System
- System Calibration at Final Test
- Runtime (Pre-patient) Calibration Using a Calibration Check Pad
- Scan Site Checking Using a Fiducial Target Hardware Related Requirements
- The Hyperspectral Scan Module shall provide at least 1000×1000×8 bits monochrome image at a frame rate of 8 frames per second or better on the USB 2.0 or IEEE 1394 (Firewire) image output.
- Acquisition of a single scan frame shall occur within one second.
- Hyperspectral Scan Subsystem shall provide region-of-interest capability; that is, the capability to select a subset of the pixels in a row and a subset of the number of columns to be analyzed.
- Hyperspectral Scan Subsystem shall provide for image binning; that is, the capability to reduce the native resolution of the input image data for displaying the data on the monitor.
- Hyperspectral Scan Subsystem shall provide the ability to set the detector gain, offset and integration time.
- Hyperspectral Scan Subsystem shall be able to set detector control parameters based on values provided in a calibration initialization file.
- Hyperspectral Scan Subsystem shall be able to flip input image data on the y (vertical or up/down) axis and on the x (horizontal or left/right) axis.
- Hyperspectral Scan Subsystem shall provide wavelength selection from a wavelength selector (LCTF, AOTF or filter wheels) from 500 nm to 660 nm.
- Hyperspectral Scan Subsystem shall be able to select wavelength in a minimum Step Size of 1 nm.

Oxy Vu-1 System User Inputs Module

The operator has the ability to control the operation of the system through the use of a keyboard and mouse. The light sources is controlled with a manual switch. General Requirements. The software allows the user to enter patient identifiers such as patient name, medical record, and date of birth. The software requires the user to log in using a username and password. The software allows the user to choose or enter the anatomical site to be scanned. The software clears prior patient info variables prior to starting the next patient.

Hardware Related Requirements
- The software supports textual user input from a keyboard
- The software supports user input from a pointing device such as a mouse OxyVu-1 System Final Test Calibration Module The OxyVu system is calibrated at manufacturing final test and each service visit. The calibration software collects hardware settings and acquires various scan data. After a successful calibration, the optimal hardware settings and calibration parameters is determined and these settings and parameters saved in the INI-files. The hardware settings are used to initialize the system during normal patient measurements and the calibration parameters are used to check system performance by the Runtime Calibration. Some milestone calibration data collected for the calibration are saved on hard disk for record and future reference. The same calibration software is also used during each scheduled service visit.

General Requirements

The system contains software to calibrate the OxyVu-1 and compute calibration parameters at Final Test and each scheduled service visit. INI-files are created to store system specific setup parameters and final test calibration data during manufacturing final test and be updated during each service visit. INI files are system files and are modified only by the authorized service personals. The unit serial number and service date are saved in the INI files. The detector settings and wavelength selector setting are saved in the setup INI file All other system related parameters are saved in the INI file. The system acquires one or more scans from the OxyVu Check Pad. Raw calibration data are stored in a subfolder corresponding to the particular patient and visit. Calibration parameters for detector and wavelength selector are saved in the calibration INI file. The software controls the OxyVu hardware to acquire a hyperspectral data cube from an OxyVu Check Pad. Calibration will fail if one or more calibration parameters do not meet the predefined values.

Hazard Related Requirements

The software prevents use of the system when it detects hardware failures and error conditions. The software determines if the measured illumination value is within tolerances. Using an OxyVu Check Pad, the software analyzes the light uniformity at each wavelength and determine if the measured uniformity is within tolerances.

Using an OxyVu Check Pad, the software analyzes distortion of the system and determine if it is within tolerances. Using an OxyVu Check Pad, the software analyzes the RMS noise value of the acquired scans and determine if it is within tolerances. Using an OxyVu Check Pad, the software analyzes whether the system is in focus within specified tolerances.

System Pre Patient Calibration Module

The OxyVu-1 system is calibrated every time before collecting patient data. A new OxyVu Check Pad is used for each patient. The calibration software collects image data for system focus, illumination power, wavelength accuracy and reuse of the OxyVu Check Pad. These data are used to verify correct instrument operation and to adjust the acquired tissue scan data. The system has to pass the pre-patient calibration prior to taking patient data.

General Requirements
- The software controls the OxyVu hardware to acquire a hyperspectral data cube from an OxyVu Check Pad.
- Software acquires and display an image to facilitate system positioning for the FOV selection.
- Software processes the OxyVu Check Pad scan to obtain a spectral and spatial check of the illumination source.
- Software processes the OxyVu Check Pad image to obtain a color check for the LCTF.
- Software processes the OxyVu Check Pad scan to obtain a focus check of the OxyVu Check Pad and check of the unique identifier barcode marking.

Pre-patient calibration will fail and prompt user if any values recorded in the OxyVu Check Pad scan are above an acceptable threshold.

The system displays the status of the ongoing calibration to the user on the system monitor If user intervention is required during the calibration sequence, the system displays user instructions required on the system display monitor. The software doe not proceed to patient measurement unless it successfully measures an OxyVu Check Pad.

Patient Tissue Oxygenation Measurement Module

Data collection from tissue requires a single use OxyVu Target placed near the center of the FOV. The system is checked during data acquisition for each site to ensure correct instrument operation. The scan data contains information related to both the tissue and the OxyVu Target. The calibration software analyzes the OxyVu Target for system focus and illumination. These data are used to verify correct instrument operation and to compensate acquired tissue image data.

General Requirements

The software requires that the OxyVu Target be placed on the tissue within the scan FOV. The system acquires tissue scans along with the OxyVu Target. The software performs image recognition and identify the OxyVu Target. The software displays a warning message if the OxyVu Target is not present in the FOV and prompt user to reposition the imaging module or reposition the Target. The software performs a check on the OxyVu Target to rule out excessive ambient lighting. The software prompts the user if excessive ambient lighting is detected. The software computes a focusing indicator from the scan and verify if it is within limits. The software prompts the user to refocus the system if the focusing indicator is outside of the limits. The software acquires a hyperspectral cube of the tissue FOV. The software stores and displays the temperature of the tissue surface as measured by the thermometer.

Tissue Oxygenation Processing Module

The raw hyperspectral image cube collected from tissue is combined with stored calibration data to process into an acceptable form. The stored and evaluated background image hypercube calibration file is subtracted from the tissue image hypercube. The stored and evaluated background image hypercube calibration file is subtracted from the OxyVu Check Pad image hypercube. The apparent absorption image hypercube, i.e., the negative logarithm of the background subtracted tissue data cube if divided by the background subtracted OxyVu Check Pad data cube is then calculated. The baseline for each spectrum in the apparent absorption data cube is forced to zero by subtracting a second order polynomial fit using data at each end of the spectrum. The baseline corrected apparent absorption spectra is then fitted with a function to determine the relative amounts of oxyhemoglobin and deoxyhemoglobin for each pixel in the original or binned image cube. Total hemoglobin and hemoglobin oxygen saturation values are determined from the oxyhemoglobin and deoxyhemoglobin values found for each pixel in the original or binned image cube.

A HSV pseudo color map is created for display that uses for the HSV planes the scaled oxyhemoglobin value, deoxyhemoglobin value, and the grey-scale image recorded at 450 nm. The HSV pseudo color map is converted to a RGB pseudo color map.

Display Output Module

The display module displays the RGB pseudo color map to the user along with values for oxyhemoglobin, deoxyhemoglobin, and hemoglobin oxygen saturation determined from a mean area located near the center of the scan. The user has the opportunity to select other areas for analysis. The system displays the RGB pseudo color scan to the user. The output display reports the patient's name, date/time of the scan, medical record, and date of birth. The output display reports the temperature of the skin measured with the thermometer. The output display reports the mean value for oxyhemoglobin measured from the default region of interest. The output display reports the mean value for deoxyhemoglobin measured from the default region of interest. The output display reports the mean value for hemoglobin oxygen saturation measured from the default region of interest.

The software allows the user to determine the mean value for oxyhemoglobin found in a user selected region. The software allows the user to determine the mean value for deoxyhemoglobin found in a user selected region. The software allows the user to determine the mean value for hemoglobin oxygen saturation found in a user selected region. The software allows the user to print the output display as a medical record.

OxyVu Software Related Design

HyperMed OxyVu comprises a console and an instrument head. The user positions and focuses the instrument head by overlapping two crossed low power light beams in the center of the field of view. The system acquires hyperspectral data, determines an approximate value for hemoglobin oxygen saturation using a classification algorithm, and presents a map of the tissue hemoglobin oxygen saturation as output for the user. The system also produces a printed report. The system is calibrated with a NIST traceable flat diffuse reflectance standard during final test and service visits. Calibration is validated prior to each patient using a disposable OxyVu Check Pad. The integrity of patient measurements are checked using an OxyVu Target.

Overall Description

The software implements the user interface module, data acquisition, data process and analysis algorithms, focusing and illumination evaluation module, pre-patient calibration and calibration checking module, and final test calibration module. The final test calibration software is used in the manufacturing process and during service visits. It is used to make pass/fail determinations of the system. All other software modules are used during patient visit to calibrate the system for proper function and acquire, process, and analyze the scan data for tissue characterization.

OxyVu Software Architecture

Figure 13:
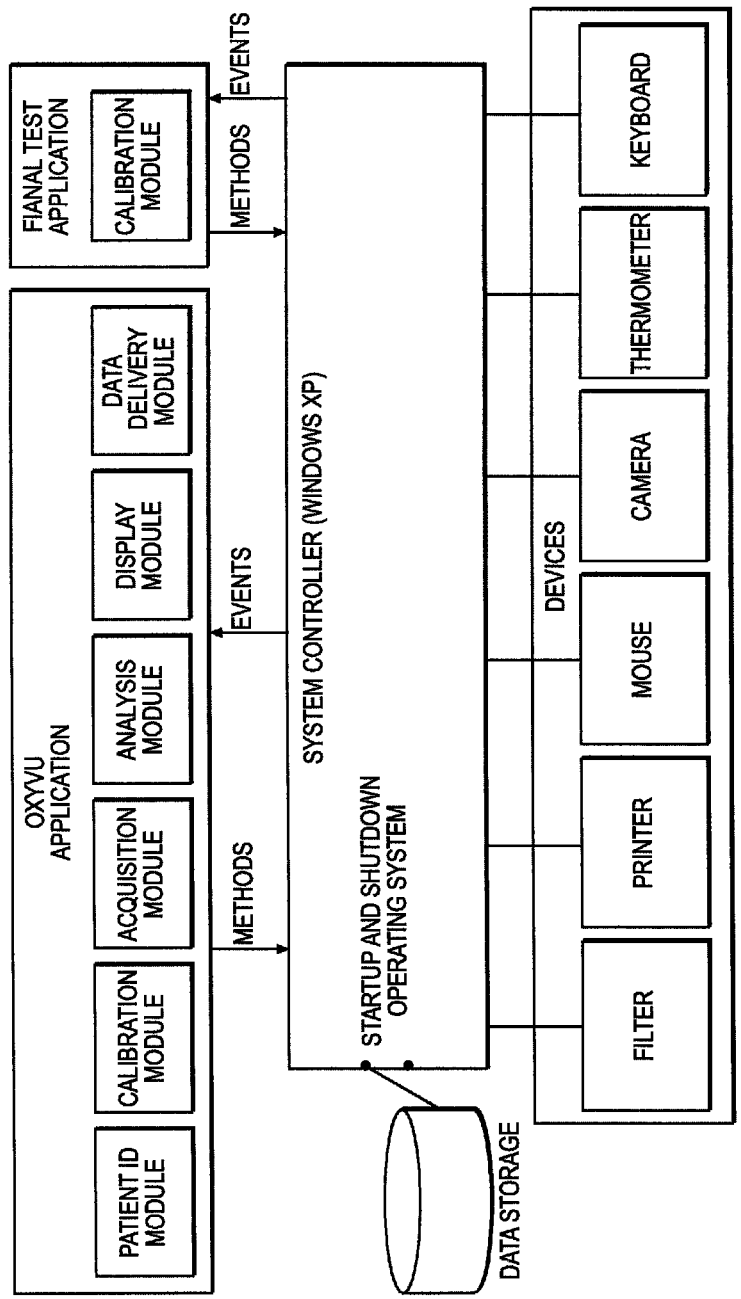
FIG. 13 OxyVu-1 Software Architecture.
Figure 14:
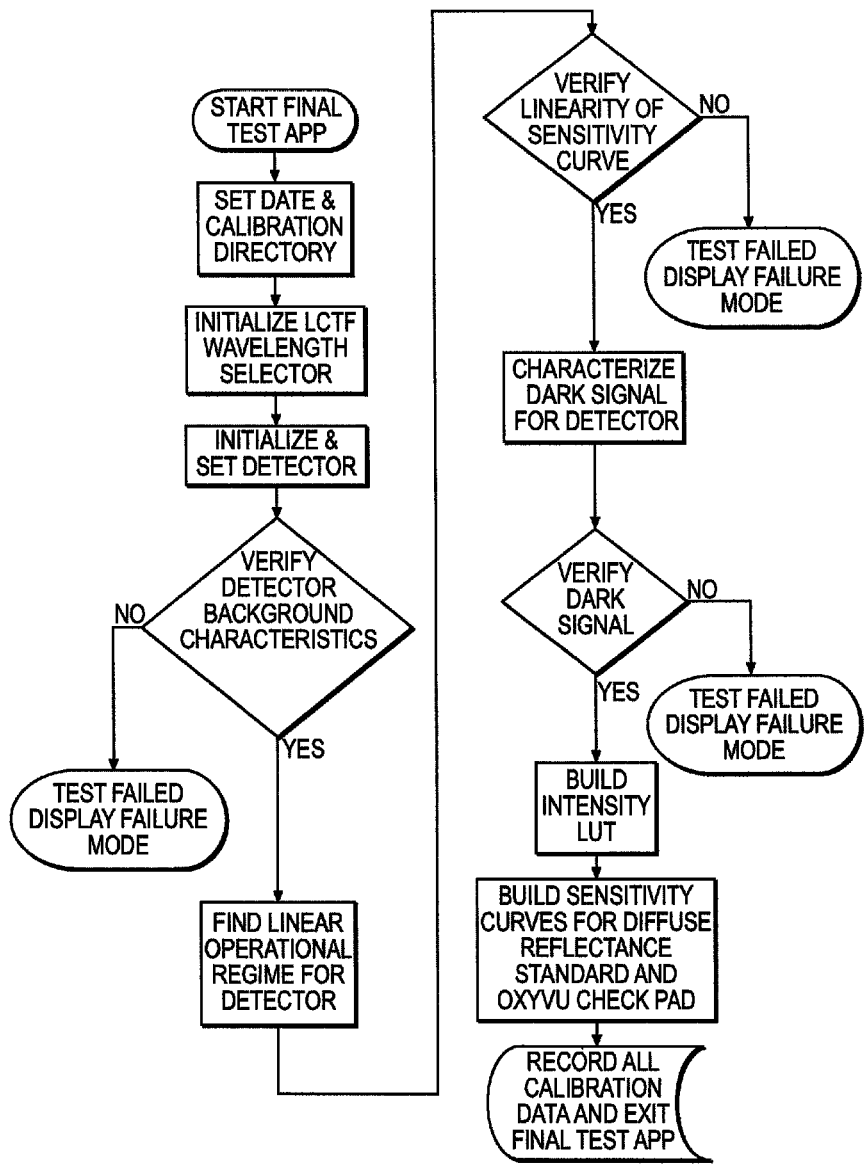
FIG. 14 OxyVu Final Test Flowchart.
Figure 15:
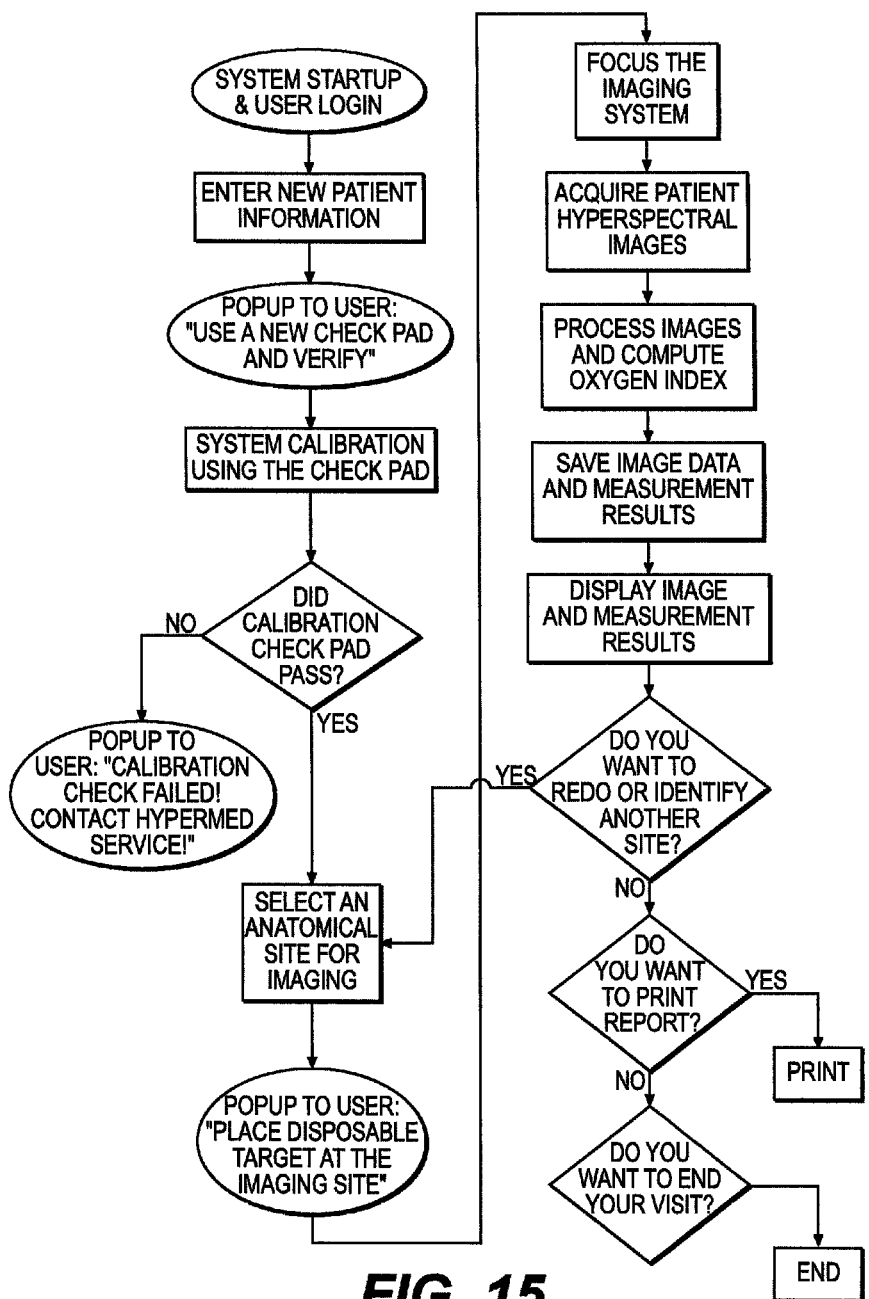
FIG. 15 OxyVu Image Data Acquisition Flowchart.

A drawing of the software architecture is shown in FIG. 13. The OxyVu application is broken down into functional modules and interfaces to hardware devices via the computer system controller and Windows XP operating system. The Final Test software is a stand alone application that interfaces to hardware devices via the computer system controller and Windows XP operating system. The Final Test software is intended to be run by trained manufacturing and service personnel and records calibration information specific to each system and stores the data on the hard drive (FIG. 14). The OxyVu application is preferably intended to be used by healthcare providers and captures hyperspectral scans from selected tissue sites and present the tissue oxygenation status for that site to the user (FIG. 15). The final output is printed to a commercial printer, stored onto the hard drive, and archive for future retrieval. The Final Test software is a stand alone application that interfaces to hardware devices via the computer system controller and Windows XP operating system. The OxyVu application is read in and use the final test data to capture, process and report tissue oxygenation status.

OxyVu System Final Test Software (See FIG. 14.)

The OxyVu-1 system is calibrated during manufacturing release and service visits. The calibration software provides for the collection of calibration and reference data. After a successful calibration, the data collected for the calibration are saved on hard disk for record and future reference. The calibration and setup results are saved in INI-files and used for initializing the system and processing the patient data during normal patient measurement. The same calibration software is also used as Runtime Calibration during each system Preventive Maintenance (PM) Service. The final test software is mostly automated and is run by starting a software executable. The calibration is performed according to the following order:

Set the date and calibration directory.
Setup the calibration and the setup structure arrays and INI files.
Initialize LCTF filters.
Initialize and set the detector.
Turn the LED lights on.
Remove cover from instrument head.
Initialize the detector.
Set the detector.
Display the background offsets and verify that odd and even rows are not separated by more than 1 count, mean background image is below 15 counts, and background histogram peaks below 15 counts.
Record the detector characteristics into the current INI files.
Find linear operational regime for imaging detector: the range of exposures where intensity changes almost linearly.
Set filter to a wavelength that provides no pixel saturation at maximal exposure. Record intensities across all exposure points.
Define exposures with the slope exceeding the threshold.
Display linearity of the detector with the threshold levels.
Verify that the sensitivity curve of the detector approximates the linear function and the slope is within the allowed range and the sensitivity curve.
Record the detector characteristics into the current INI files.
Characterize dark radiation images for the detector.
Close instrument head aperture with a cover.
Scans at set exposures that cover entire allowable exposure range.
Record scans corresponding to the minimal and maximal exposures onto the hard drive.
Display characteristics of the dark radiation scans: dependence of mean image amplitude and warm pixels vs. exposure; and deviation of dark radiation images from the linear approximation.
Verify that the mean scan amplitude barely depends on exposure, the number of watin pixels is below 1%, and dark intensity for most pixels linearly depends on exposure.
Record the detector characteristics into the current INI files.
Build look-up-table, LUT: dependence of pixel intensity on exposure.
Remove cover from the instrument head.
Set filter to a wavelength that provides no saturation at maximal exposure.
Acquire multiple scans at each exposure in the allowed exposure range to gain good statistical results.
For an ROI in the middle of the scan, construct dependence of mean intensity on exposure.
Define LUT as 5th order polynomial.
Record the detector characteristics into the current INI files.
Build sensitivity curves.
Define an array of wavelengths covering entire operational wavelength range of the system.
Define sensitivity curve for reflectance standard.
Focus system on the reflectance standard.
Acquire hyper-cube.
Store hyper-cube onto the hard drive.
Record wavelength, exposure, and number of acquisitions per scan for reflectance standard into the current INI files.
Define sensitivity curve for the OxyVu Check Pad.
Focus system on the OxyVu Check Pad.
Acquire hyper-cube.
Store hyper-cube onto the hard drive.
Record wavelength, exposure, and number of acquisitions per image for OxyVu Check Pad into the current INI files.
Complete the calibration and the setup INI files by processing sensitivity data files off standard reflector and OxyVu Check Pad.

OxyVu Application Calibration Module

The Runtime Calibration module is responsible for performing system checks and calibrations required for acquiring valid patient data. The current performance parameters of the system are compared with the performance parameters from the Final Test or previous Preventive Maintenance (PM). If any of these performance parameters are outside of the predefined range, the software prevents user to continue use the system and display a warning message to call support personal for help. Some test modules performed during the PM are repeated during runtime calibration and the results are compared with the PM values. Specific tests may have different failure limits during the runtime calibration than they would during the PM calibration. Differences are noted for the appropriate tests. All tests performed are done prior to patient testing using the OxyVu Check Pad. The user is prompted to place a new OxyVu Check Pad and focus the instrument to begin the calibration. For each measurement site, a small OxyVu Target is used as a fiducial mark. This target is also used to determine the ambient light and check for focus and motion artifacts. For the pre-patient calibration, hyperspectral data are acquired with specified parameters. The first test to be performed is the illumination power and uniformity. The user is prompted to turn off ambient room light. This test is perform with the following steps:

Crop the acquired image to the region specified in the *INI file—this region corresponds to a part of the white portion of the calibration pad. Subtract the previously recorded dark radiation from the image. Compute the reflectance. Fit a second order surface to the image data at each wavelength. Compute the maximum deviation between the fitted surfaces and ideal calibration surfaces. Compare the computed maximum deviation to a threshold parameter. If it exceeds the parameter then the calibration fails, otherwise the calibration succeeds. Te second test to be performed is the wavelength accuracy. It is based on comparing the colored region in the acquired image to the information recorded in the *INI file. This test is perform in the following steps:

Crop the acquired image to the region specified in the *INI file—this region corresponds to a colored portion of the calibration pad.
Subtract the previously recorded dark radiation from the image.
Compute the reflectance.
Compute the reflectance amplitude averaged over ROI.
Compute the difference between decimal logarithm of the acquired average image values and logarithm of the calibration values.
Convert the computed difference to percentages and compare to the specified threshold. If the difference exceeds the threshold then the calibration fails, otherwise the calibration succeeds.
Repeat the above steps for any other colored calibration area.

The third test to be performed is the image focus test. This test performs the following steps:
  Crop the acquired image to the region specified in the *INT file—this region corresponds to a part of the barcode portion of the calibration pad and to the specified wavelengths.
  Compute normalized auto correlation of the image.
  Compute the half width at half amplitude of the image and compare it to the specified threshold values. If the half widths are smaller than the thresholds then the calibration succeeds, otherwise the calibration fails.

The fourth test to be performed is the Barcode Check. The reading of the barcode is decoded and if found to be invalid prompts the user to replace the OxyVu Check Pad. This procedure is preferably performed every time before collecting patient data. Find the upper edge of OxyVu Check Pad and determine the rotation of the target and realign the pad based on the rotation amount.

Identify the Barcode Area, BC(m,n) on the OxyVu Check Pad
  If a valid barcode area cannot be found in the scan, prompt the user to place a new, valid OxyVu Check Pad. Decode barcode data from the scan. Validate barcode data to stored data. If a valid barcode number cannot be found, prompt the user to place a valid OxyVu Check Pad.

OxyVu System User Interface Module (See FIG. 15).
  User Log On—The system is password protected. Upon starting the OxyVu application, the user is prompted to enter a username and password. The system checks the Operator ID and Password to ensure that they match the product's database. If they fail to match, the user is prompted to re-input their Operator ID and Password. For each patient (identified by their Patient ID), the operator is required to enter their Operator ID for follow up and tracking purposes. The operator must be prompted to insert the calibration pad to calibrate the device. After clicking on a button on the user interface, the calibrator pad is automatically checked to determine whether it is properly positioned and meets the quality specifications. If the pad passes the test, the operator can move to the next step in the process. The operator is asked to place the calibrator pad in the device. The operator then presses the "Next" button to test the calibrator pad.

Figure 16:
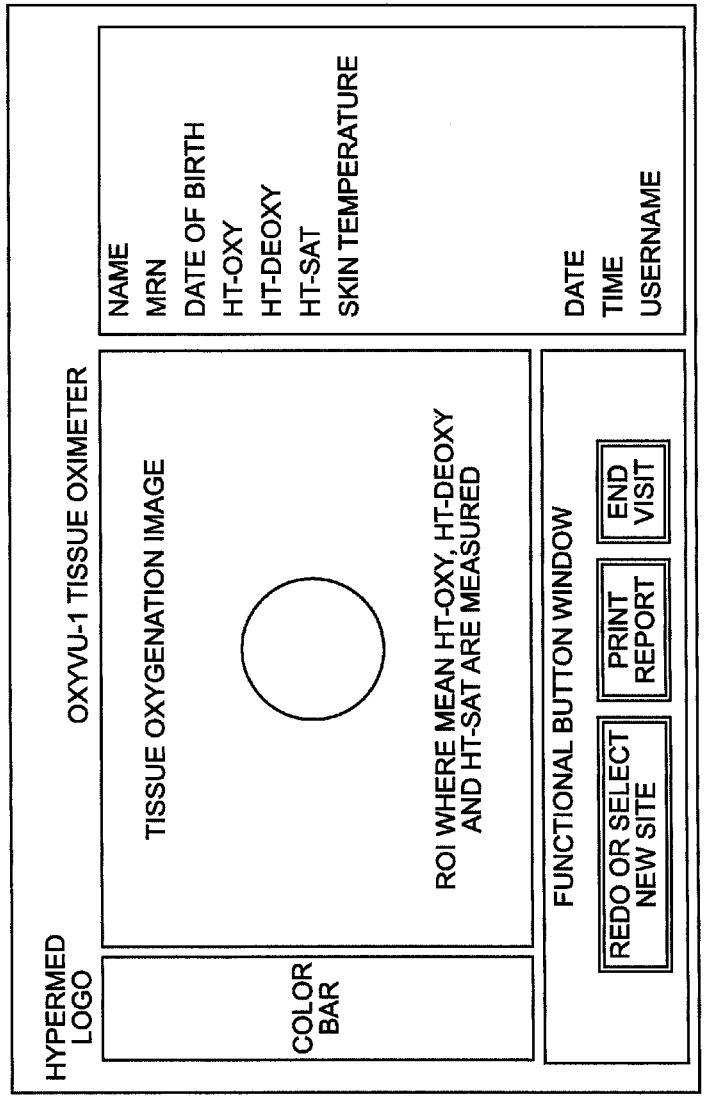
FIG. 16 OxyVu-1 Tissue Oxygenation Measurement Display.

OxyVu Output Display Module
  The block diagram of FIG. 16 describes the different panels on the output display window. The diagram shows the functional property of the output display window. The exact location and style may vary in different products.

COTS Software
  Software Function: Intended use—The COTS software provides the operating environment and hardware interface for the OxyVu software. The OS and drivers provide an industry standard application programming interface (API) to interact with the hardware. Device error control is provided by the OxyVu software and checks the operation of the COTS software. The OxyVu software informs the user for any COTS error conditions. The COTS software is tested as configured for its intended use Software Control
  Access to the operating system shall be password protected. Only authorized service personnel have the ability to modify the software configuration of the device. Maintenance of the COTS configuration is controlled by 3-00000 assembly procedure COTS Software is controlled using Subversion Revision Control Software.

Maintenance and Life Cycle Support
  Each COTS software application is assigned a specification number under Document Control. To modify the version of COTS software being used, a Change Order is required which includes a description of the change and testing to support the change. When the change is made, software testing is performed by Product Assurance to ensure that the change did not adversely impact the device safety and function Summary/Results
  The pre-patient calibration consists of acquisition of hyper-cube off OxyVu Check Pad disposable calibrator, and verifying that system perfoms in accordance to specifications. The acquired data are processed using three software programs: is White.m, is Color.m, and is Focus.m. The three codes are tested prior release with the three testing programs: test is White.m, test is Color.m, and test is Focus.m, correspondingly.

Two types of statements are typically tested: positive and negative. The table above starts with a positive test of white light illumination. Given the "gold standard data" for threshold, hypercube, and system state as input parameters, the test has to provide expected result "true." Similarly, the other two positive tests are outlined in row 3 and 5 of the table, with expected results "true" and "true". The negative test is based on providing a condition prior known to cause an expected failure result. For example, the test is White.m (second row of the table) should give out "false" given an unreasonably low threshold value. A similar case is shown in the last row of the table with the code test is Focus.m. Another example of negative testing (fourth row of the table) intentionally inputs insufficient number of parameters. The expected result is an error message "Input argument "hsiSystem" is undefined" and is compared to the actual result to determine validity of the software programs.

Other embodiments and uses of the invention is apparent to those skilled in the art from consideration of the specification and practice of the invention disclosed herein. All references cited herein, including all publications, U.S. and foreign patents and patent applications, are specifically and entirely incorporated by reference including Provisional Application No. 60/817,340, U.S. patent application Ser. No. 11/692,131 entitled "Hyperspectral Imaging of Angiogenesis" filed Mar. 27, 2007, U.S. patent application Ser. No. 11/522,529 entitled "Disposable Calibration Fiducial Mark for Hyperspectral Imaging" filed Sep. 18, 2006, U.S. patent application Ser. No. 11/507,043 entitled "Hyperspectral Technology for Assessing and Treating Diabetic Foot and Tissue Disease" filed Aug. 21, 2006, U.S. patent application Ser. No. 11/396,941 entitled "Hyperspectral Imaging in Diabetes and Peripheral Vascular Disease" filed Apr. 4, 2006, U.S. patent application Ser. No. 11/288,410 entitled "Medical Hyperspectral Imaging for Evaluation of Tissue and Tumor" filed Nov. 29, 2005, and U.S. patent application Ser. No. 11/319,225 entitled "Hyperspectral/Multispectral Imaging in determination, Assessment and Monitoring of Systemic Physiology and Shock" filed Dec. 28, 2005. It is intended that the specification and examples be considered exemplary only with the true scope and spirit of the invention indicated by the following claims.

The invention claimed is:
1. A no invasive, tissue oxygenation measurement system comprising:
  (A) a hyperspectral/multispectral imaging camera configured to acquire a series of images of a tissue of a subject, the series of images forming a hyperspectral imaging cube;
  (B) one or more processors in electronic communication with the hyperspectral/multispectral imaging camera;
  (C) a memory storing one or more programs for execution by the one or more processors; and

(D) a display configured to display a two-dimensional image of tissue oxygenation of a tissue of a subject imaged by the hyperspectral/multispectral imaging camera, wherein the one or more programs comprise:

instructions for resolving a plurality of absorption signals from the series of images of the tissue of the subject, instructions for correcting background noise from each respective absorption signal in the plurality of absorption signals by subtracting the contribution provided by melanin and the losses provided by diffuse scattering from the respective absorption signal, wherein the contribution provided by melanin and the losses provided by diffuse scattering to the plurality of tissue oxygenation measurements are collectively modeled as a second order polynomial, thereby forming a plurality of corrected absorption signals, instructions for determining a plurality of tissue oxygenation measurements for the tissue of the subject based on the plurality of corrected absorption signals, and instructions for forming the two-dimensional image of tissue oxygenation from the plurality of corrected tissue oxygenation measurements.

2. The system of claim 1, wherein the plurality of tissue oxygenation measurements comprise: a value for oxyhemoglobin and a value for deoxyhemoglobin.

3. The system of claim 1, wherein the two-dimensional image of tissue oxygenation is configured to be viewed pixel-by-pixel, as a region of interest, or for a viewing area.

4. The system of claim 1, further comprising one or more devices from the group consisting of system electronics, a keyboard, a pointing device and a printer, wherein the one or more devices are in electronic communication with the hyperspectral/multispectral imaging camera.

5. The system of claim 1, further comprising a hyperspectral instrument head with a support arm, wherein the hyperspectral instrument head comprises a broadband illuminator, the camera, and a spectral filter for collecting a three-dimensional matrix of spectral measurements in the form of a hyperspectral imaging cube.

6. The system of claim 5, wherein the hyperspectral instrument head is configured to be positioned 17 inches from the tissue site of interest.

7. The system of claim 5, wherein the broadband illuminator is configured to produce polarized visible light.

8. The system of claim 1, wherein the two-dimensional image has at least 0.1 mm spatial resolution within a field of view.

9. The system of claim 1, further comprising a check pad and a target, wherein
the target is configured for use as a fiduciary mark for image registration and focusing when placed within an intended field of view at the tissue; and
the check pad and the target are configured to be placed within the view of the hyperspectral/multispectral imaging camera prior to acquisition of the series of images of the tissue.

10. The system of claim 1, wherein the two-dimensional image has a resolution of 50 microns.

11. The system of claim 1, wherein the system is configured to acquire the series of images of the tissue site of interest on the subject within 2 seconds.

12. The system of claim 1, wherein the system is configured to not physically contact said subject.

13. The system of claim 1, wherein the tissue site of interest comprises or is near a wound or an ulcer.

14. The system of claim 1, wherein the system is configured to detect a reduced blood flow ischemia state in the subject.

15. The system of claim 1, further comprising a hard drive disk onto which data or displayed information obtained from the system is stored, wherein the hard disk drive is in electrical communication with the one or more processing units.

16. The system of claim 15, further comprising software non-transitorily stored on the hard drive disk to perform a system integrity check.

17. The system of claim 16, wherein the system integrity check comprises calibration, verification of consistency of the software and the data, validation of algorithm software using a known calibration scheme, and verification of operation and functionality of the hard drive disk.

18. The system of claim 1, wherein the system is configured to measure diffusely reflected backscattered light at 15 or more wavelengths between 500 nm and 660 nm.

19. The system of claim 18, wherein the backscattered light is measured at increments of at least 5 nm.

20. The system of claim 1, wherein the hyperspectral/multispectral imaging camera comprises a two-dimensional CMOS detector.

21. The system of claim 1, further comprising a liquid crystal tunable filter, and wherein the liquid crystal tunable filter is in optical communication with hyperspectral/multispectral imaging camera.

22. The system of claim 1, wherein the display is configured, in response to user selection of a region of the two-dimensional image of tissue oxygenation, to display an average value of a calculated diagnostic feature of the selected region.

23. The system of claim 22, wherein the calculated diagnostic feature is selected from the group consisting of:
a value for oxyhemoglobin;
a value for deoxyhemoglobin;
a value for percent oxygen saturation;
an automatic ulcer border mapping;
a semiautomatic ulcer border mapping;
a value for ulcer size;
a value for ulcer depth;
an ulcer healing index; and
an ulcer prediction index.

24. The system of claim 22, wherein the diagnostic feature comprises an ulcer healing index and wherein the ulcer healing index comprises any one or more of the group consisting of:
a comparison of one or more values inside an ulcer to one or more values outside the ulcer;
a comparison of one or more values outside the ulcer to one or more values measured from the subject's forearm;
a comparison of one or more values outside the ulcer to one or more values measured on a previous visit of the subject;
a comparison of one or more values inside or outside the ulcer to one or more pieces of clinical data; and
a comparison of a response of one or more values inside or outside the ulcer to leg dependency, blood pressure cuff induced ischemia, exercise induced ischemia, or administered oxygen.

25. The system of claim 22, wherein the diagnostic feature comprises an ulcer prediction index and wherein the ulcer prediction index comprises any one or more of the group consisting of:
a comparison of one or more values from a site of interest to one or more values outside the site of interest;

a comparison of one or more values outside the site of interest to one or more values measured from the forearm;

a comparison of one or more values outside the site of interest to one or more values measured on a previous visit of the subject;

a comparison of one or more values inside or outside the site of interest to one or more pieces of clinical data; and a comparison of one or more values inside or outside the site of interest to leg dependency, blood pressure cuff induced ischemia, exercise induced ischemia, or administered oxygen.

26. The system of claim 1, wherein the instructions for correcting background noise comprise quantifying the contribution provided by melanin and the loss provided by diffuse scattering by fitting the second order polynomial to the plurality of absorption signals for each respective image in the series of images of the tissue of the subject.

27. The system of claim 26, wherein the second order polynomial has the form:

$$(b_2(x,y)\lambda^2 + b_1(x,y)\lambda + b_0(x,y))$$

wherein $b_0$, $b_1$ and $b_2$ are coefficients determined by minimizing the squared difference between the term $(b_2(x, y)\lambda^2 + b_1(x, y)\lambda + b_0(x, y))$ and the plurality of absorption signals determined for the image acquired at each wavelengths ($\lambda$) by the hyperspectral/multispectral imaging camera at coordinates (x, y) of the tissue site on the subject.

28. The system of claim 1, wherein the instructions for correcting background noise comprise subtracting the contributions provided by melanin and the losses provided by diffuse scattering from the absorption signal $A_T(\lambda,x,y)$ to form the plurality of corrected absorption signals $A_H(\lambda,x,y)$ by applying the second order polynomial:

$$A_H(\lambda,x,y) = A_T(\lambda,x,y) - (b_2(x,y)\lambda^2 + b_1(x,y)_2 b_0(x,y))$$

wherein, $b_0$, $b_1$ and $b_2$ are coefficients, $\lambda$ is the wavelength of the absorption signal and x, y are positional coordinates on the tissue of the subject.

29. The system of claim 28, wherein absorption signals $(A_T)(\lambda,x,y)$ are determined by comparing the reflected light from the tissue of the subject to a background illumination signal using the algorithm:

$$A_T(x, y, \lambda) = -\log_{10}\left(\frac{I_t(x, y, \lambda) - B'(x, y, \lambda)}{I_0(x, y, \lambda) - B'(x, y, \lambda)}\right),$$

wherein, $I_t$ and $I_o$ are reflective intensities collected during acquisition of the series of images from the tissue of the subject at (x,y), and B' is a background illumination signal recorded with a closed camera aperture.

30. The system of claim 28, wherein the instructions for determining a plurality of tissue oxygenation measurements comprise determining a total hemoglobin level (HT-THb) by calculating the total absorbance of $A_H$ in the wavelength region between 530 nm and 590 nm.

31. The system of claim 1, wherein the instructions for determining a plurality of tissue oxygenation measurements comprise determining relative contributions of oxyhemoglobin (oxyHb($\lambda$)) and deoxyhemoglobin (deoxyHb($\lambda$)) to a corrected absorption signal resolved at wavelength $\lambda$ at a position (x,y) on the tissue of the subject by fitting the equation:

$$c_3(x,y) \times deoxyHb(\lambda) \times K(\lambda) + c_2(x,y) \times oxyHb(\lambda) \times K(\lambda) + c_1(x,y) \times K(\lambda) + c_0(x,y)$$

to the corrected absorption signal, wherein $c_0$, $c_1$, $c_2$ and $c_3$ are coefficients, and $K(\lambda) = (\lambda - 500)/300$.

32. The system of claim 31, wherein the instructions for determining a plurality of tissue oxygenation measurements further comprise determining a percent hemoglobin oxygen saturation HTSat(x,y) using the equation:

$$HTSat(x, y) = \frac{c_2(x, y)}{c_2(x, y) + c_3(x, y)} \times 100\%.$$

33. The system of claim 31, wherein the instructions for determining a plurality of tissue oxygenation measurements further comprise determining approximate levels of oxyhemoglobin HTOxy(x,y) and deoxyhemoglobin HTDeoxy(x,y) for the tissue of the subject using the equations:

$$HTOxy(x, y) = \frac{HTSat(x, y) \times HTTHb(x, y)}{100}$$

and $$HTDeoxy(x,y) = (HTTHb(x,y) - oxyHB(x,y)).$$

* * * * *